United States Patent
Murray et al.

(10) Patent No.: US 12,324,914 B2
(45) Date of Patent: *Jun. 10, 2025

(54) STRUCTURAL INTEGRATION AND ENHANCED CONTROL OF FUNCTIONAL ELECTRICAL STIMULATION IN AN EXOSKELETON DEVICE

(71) Applicant: Ekso Bionics Holdings, Inc., San Rafael, CA (US)

(72) Inventors: Spencer Murray, Aurora, OH (US); Don Truex, Murfreesboro, TN (US); Michael Goldfarb, Franklin, TN (US); Scott Morrison, Mount Pleasant, MI (US); Ryan Farris, Mechanicsburg, PA (US)

(73) Assignee: Ekso Bionics Holdings, Inc., San Rafael, CA (US)

( * ) Notice: Subject to any disclaimer, the term of this patent is extended or adjusted under 35 U.S.C. 154(b) by 316 days.

This patent is subject to a terminal disclaimer.

(21) Appl. No.: 18/045,956

(22) Filed: Oct. 12, 2022

(65) Prior Publication Data

US 2023/0075154 A1   Mar. 9, 2023

Related U.S. Application Data

(63) Continuation of application No. 16/770,104, filed as application No. PCT/US2018/017936 on Feb. 13, 2018, now Pat. No. 11,654,280.

(51) Int. Cl.
*A61N 1/36* (2006.01)
*A61H 3/00* (2006.01)

(52) U.S. Cl.
CPC .......... *A61N 1/36003* (2013.01); *A61H 3/00* (2013.01); *A61N 1/36031* (2017.08);
(Continued)

(58) Field of Classification Search
CPC .................. A61N 1/36003; A61N 1/36031
See application file for complete search history.

(56) References Cited

U.S. PATENT DOCUMENTS

| 5,121,747 A | 7/1992 | Andrews |
| 9,456,918 B2 | 10/2016 | Siegler et al. |

(Continued)

FOREIGN PATENT DOCUMENTS

| CN | 103655122 A | 3/2014 |
| EP | 0 339 665 A2 | 11/1989 |

(Continued)

OTHER PUBLICATIONS

International Search Report and Written Opinion for corresponding International Patent Application No. PCT/US2018/017936 mailed on Jul. 4, 2019.

(Continued)

*Primary Examiner* — Joseph M Dietrich
(74) *Attorney, Agent, or Firm* — Renner, Otto, Boisselle & Sklar, LLP

(57) ABSTRACT

An integrated functional electrical stimulation (FES) system includes a component of a mobility assistance device, and an FES system mounted within the component. The FES system includes an FES stimulator that is embedded within the component, and a plurality of FES jacks that are electrically connected to the FES stimulator and are located on the component. The FES jacks are configured to receive a plurality of FES electrodes, and an electrical stimulation output from the FES stimulator is conducted through the FES jacks to the FES electrodes. In a wireless embodiment, the FES stimulator is configured to wirelessly transmit a control signal for applying an electrical stimulation output to the plurality of FES electrodes, and the FES jacks are eliminated. The FES stimulator may be embedded within a back portion of the hip component of an exoskeleton device, (Continued)

and in the wired embodiment the FES jacks are located on wing portions of the hip component.

20 Claims, 13 Drawing Sheets

(52) U.S. Cl.
CPC .. *A61H 2201/10* (2013.01); *A61H 2201/5097* (2013.01); *A61H 2205/088* (2013.01); *A61H 2230/605* (2013.01)

(56) References Cited

U.S. PATENT DOCUMENTS

| | | |
|---|---|---|
| 2006/0206167 A1 | 9/2006 | Flaherty et al. |
| 2013/0197408 A1 | 8/2013 | Goldfarb et al. |
| 2014/0171838 A1 | 6/2014 | Aleksov et al. |

FOREIGN PATENT DOCUMENTS

| | | |
|---|---|---|
| WO | 2012/044621 A1 | 4/2012 |
| WO | 2017/035512 A1 | 3/2017 |

OTHER PUBLICATIONS

Rudi Kobetic et al.; "Development of hybrid orthosis for standing, walking, and stair climbing after spinal cord injury;" Journal of Rehabilitation Research & Development, vol. 46, No. 3; pp. 447-462; 2009.

STRUCTURAL INTEGRATION AND ENHANCED CONTROL OF FUNCTIONAL ELECTRICAL STIMULATION IN AN EXOSKELETON DEVICE

RELATED APPLICATIONS

This application is a continuation application of U.S. application Ser. No. 16/770,104 filed Jun. 5, 2020, which is a national phase of International Application No. PCT/US2018/017936 filed Feb. 13, 2018 and published in the English language, the contents of which are incorporated here by reference.

FIELD OF INVENTION

The present invention relates generally to the use of functional electrical stimulation (FES) in combination with a mobility assistance device, such as for example a legged mobility device or "exoskeleton" device, and particularly enhanced control of an FES system structurally integrated into such an exoskeleton device.

BACKGROUND OF THE INVENTION

Individuals with spinal cord injury and other impairments of the lower limbs often suffer from muscular atrophy, muscle spasms, reduced circulation, and reduced range of motion. Regular application of functional electrical stimulation (FES) to the lower limbs has been shown to help reduce many of these symptoms. Traditional FES systems achieve stimulation of the user's muscles via application of a stimulating current to surface electrodes applied to the user's skin. Because of the benefits of FES, therapy devices have been developed that introduce FES in combination with device operation. Examples include FES therapy bikes, FES steppers, and other types of like exercise style devices. Such devices, however, necessitate a high level of muscular capability, and further are limited in their ability to provide mobility to the user due to the fixed-position nature of these types of devices. A device that could permit full mobility to different locations while providing FES would be preferred in many scenarios, as this would allow the user to continue their daily activities while receiving FES treatment.

For persons with severe impairments to mobility, powered mobility assistance devices have been developed. Powered mobility assistance devices incorporate actuators and drive motors associated with a power supply to assist with locomotion. These powered orthoses have been shown to increase gait speed and decrease compensatory motions, relative to walking without powered assistance, and can permit walking even for a severely impaired user. Examples of powered orthoses are known; for example, WO 2010/044087, US 2010/0094188, and U.S. Pat. No. 8,096,965 disclose a powered exoskeleton bracing system/exoskeleton bracing system.

Due to the limitations of devices like the stationary FES steppers and bikes, attempts have been made to develop more mobile FES systems, including using FES systems in combination with an exoskeleton device. Such attempts typically have focused on combining a pre-existing FES system with a pre-existing exoskeleton device. This type of retrofitting has proven deficient, as the combination has required an external data tether which plugs into the FES stimulator and which, in turn, outputs multiple channels of stimulation over electrode leads which lead from the FES stimulator box back to the surface electrodes on the user's skin. The system is therefore inconvenient to use, requires a helper person to carry the large FES stimulator box, and is difficult and time consuming to assemble and configure.

There are additional issues that have arisen in connection with combining FES and exoskeleton systems. There are difficulties in using these systems; for example wires tangle, electrodes disconnect or are damaged, and the like due to increased mobility. There also are limitations on the range of muscles that can be stimulated through the skin. For example, body fat can interfere with the electrical stimulation, and only muscles with nerves near the skin surface can be stimulated. These deficiencies make the use of surface electrodes non-ideal with conventional exoskeleton devices. There accordingly have are been alternative systems in which transcutaneous electrodes are inserted into the muscle through the skin and connected to a power source outside the body to improve FES performance. Systems using transcutaneous electrodes, however, can cause issues with comfort and increase the likelihood of infection in the user. Deeper implantable electrodes may alleviate these issues by placing an electrode at an internal location of stimulation, such as next to the stimulated nerve through a surgical procedure. Wires are then routed through the body to a central stimulator that is implanted near the skin surface, which is charged inductively at regular intervals, and which stimulates in response to notifications from a unit external to the body.

Advances in technology for implantable electrodes involve inserting the electrodes through a needle in a minimally-invasive procedure, which function without the requirement for wires routed through the body. Rather, these implantable systems include individualized power sources, and in some versions of the technology the system is inductively powered and does not contain a power supply, and stimulators. Such systems, however, have not been combined with exoskeleton devices to permit FES treatment of a severely impaired person while using such exoskeleton device for mobility assistance.

SUMMARY OF THE INVENTION

The present invention is directed to configurations for structural FES integration into an exoskeleton device. An FES system integrated into an exoskeleton device provides additional channels of electrical stimulation without the need of a hefty external stimulator or an external communications tether. Embodiments of the structural FES integration system integrate a ten channel stimulator into an exoskeleton device to provide a convenient robotic system capable of providing legged mobility as well as FES, by which a user simultaneously attains the benefits of both FES and the mobility assistance via the exoskeleton device. This pairing is synergistic. Conventional FES systems rely solely on the user's stimulated muscles, and the user therefore may swiftly fatigue when using electrical stimulation alone. The further integration of the FES system into the exoskeleton device permits the exoskeleton device to supplement user effort when stimulation of the user's muscles does not provide adequate power to achieve an appropriate gait. In this manner, control methods may be executed to balance user effort via FES versus device assistance by the exoskeleton joint components as warranted for user strength and performance goals. Both wired and wireless FES integration systems are described.

In exemplary embodiments of an integrated FES system, a printed circuit board (PCB) FES stimulator and FES jacks are installed in a hip component of the exoskeleton device. The PCB FES stimulator includes a microprocessor to control the electrical stimulation, and an electrical transformer that modifies the electrical output to make the electrical output suitable for stimulation. The stimulator can be powered by the exoskeleton battery, and mounted in a cavity in the hip piece of the exoskeleton device via dedicated attachment points The attachment points can be configured, for example, as openings for grommets or screws, so that the FES stimulator is fully contained within the hip component. The FES stimulator includes a communications port so that the exoskeleton's electronics can provide information to synchronize electrical stimulation with exoskeleton actions (e.g. stepping or standing up). Settings and other information from a mobile application for controlling the exoskeleton device can be received via wireless communication by the FES stimulator, or received by the exoskeleton control system and transferred to the FES stimulator from the exoskeleton control system via electrical wiring that runs through the hip component of the exoskeleton device.

The FES stimulator outputs up to ten channels of electrical stimulation to the FES electrodes. In a wired configuration, electrodes are connected to the FES simulator by connection of the electrodes to FES jacks incorporated into the hip component of the exoskeleton device. Wiring from the FES jacks in turn is routed internally through the hip component to the FES stimulator to minimize external wiring. The FES jacks may include light-emitting diodes (LEDs) that can light under a number of different circumstances to provide various indications to the user. In one example of a light indicator scheme, the FES jacks light when a corresponding channel is being stimulated, the jacks blink when settings are being modified for that channel or when performing a test function for that channel, and the jacks blink rapidly when the stimulator attempts to stimulate but no complete circuit is detected (i.e., an electrode pad has come loose, or the electrode is unplugged from the jack).

In other embodiments, a wireless integrated FES system is provided. In a wireless configuration, the integrated FES stimulator is outfitted with a wireless transmitter that communicates stimulation control signals remotely to a centralized stimulator box that stimulates the FES electrodes, or the wireless transmitter transmits stimulation control signals directly to distributed stimulating-electrodes having their own communications and power elements. In this embodiment, the PCB FES stimulator board includes a microprocessor, attachment points, and an exoskeleton communications port comparably as in the wired configuration. A wireless configuration, in contrast, lacks the electrical transformer as the components inducing the electrical current would be distributed with the electrodes and powered by induction operations. Installation of a wireless embodiment of the FES stimulator in the cavity of the exoskeleton hip component also permits elimination of the additional FES jacks formed in the hip component, as stimulation control signals would be transmitted wirelessly from the FES stimulator either to a centralized implanted stimulator box or to the implanted FES electrodes in a distributed network configuration. The various components in the wireless configuration may be powered or charged by induction.

As aspect of the invention, therefore, is an integrated FES system that integrates an FES system into a mobility assistance device, such as for example a legged mobility exoskeleton device. In an exemplary embodiment, an integrated FES system includes a component of a mobility assistance device, and an FES system mounted within the component of the mobility assistance device. The FES system includes an FES stimulator that is embedded within the component of the mobility assistance device, and a plurality of FES jacks that are electrically connected to the FES stimulator and are located on the component of the mobility assistance device. The FES jacks are configured to receive a plurality of FES electrodes, and an electrical stimulation output from the FES stimulator is conducted through the FES jacks to the FES electrodes. The component of the mobility assistance device may be a hip component of a legged mobility exoskeleton device including the hip component, a left leg component, and a right leg component. The FES stimulator is embedded within a back portion of the hip component, and the FES jacks are located on wing portions of the hip component.

In an alternative embodiment, the integrated FES system is wireless. In the wireless configuration, the FES stimulator is embedded within the component of the mobility assistance device, and is configured to wirelessly transmit a control signal for applying an electrical stimulation output to a plurality of FES electrodes. The wireless FES stimulator may be embedded within a back portion of the hip component of an exoskeleton device. The FES system may include a centralized stimulator and power hub that receives the control signal from the FES stimulator and outputs the electrical stimulation output to multiple networked FES electrodes, or the FES stimulator may be configured to transmit the control signal to multiple non-networked distributed FES electrodes including embedded power and communication components within each electrode.

The present invention further is directed to enhanced FES control in an exoskeleton device with an internal FES stimulator that is structurally integrated into an exoskeleton device. The systems and methods of the present invention provide for fully configurable muscle group channels. The integrated FES system incorporates up to ten channels of stimulation with stimulation profiles available for sixteen different muscle groups. Users can enable or disable each of the ten provided channels as desired. Any of the muscle groups may be selected for use on any channel. The stimulation profile, including pulse width, pulse amplitude, and/or pulse frequency, may be independently adjusted for each of the ten channels. The channels may be assigned and controlled using a mobile application for control of the exoskeleton device, which is modified to permit specific FES control including, for example, enabling and disabling certain channels, muscle group selection configuration, and various additional FES settings adjustments. The FES control, therefore, can be performed wirelessly via such a mobile application running on a mobile device such as smartphone, tablet computer, laptop computer, or comparable.

The present invention incudes dynamic functional FES control, by which adjustments to the FES parameters can be made in real time as the user continues to walk, permitting clinicians or other users to immediately alter parameters in response to observed behavior or data reported via the mobile application. As part of the dynamic functional FES control, automatic adjustment of stimulation is performed. The FES control applies and alters the timing of when FES is provided to ensure that the user's muscles contribute to gait. For each muscle group, the FES system selects an appropriate window for stimulation during the gait cycle. This window is expanded and contracted as necessary during an over-ground gait when the speed of the exoskeleton device changes. This adjustment is performed automatically, and does not require any intervention on the part of the user or clinical helper. With this enhanced timing of FES relative to the user gait as measured by the performance of the exoskeleton device, as referenced above the control methods may be executed to balance user effort by FES versus device assistance by the exoskeleton joint components as warranted for user strength and performance goals.

An aspect of the invention is a control method of controlling a mobility assistance device having a plurality of mobility device components including at least one actuator component that drives at least one joint component. In exemplary embodiments, the control method comprises the steps of: providing said mobility assistance device, said mobility assistance device further including a control system for controlling operation of the mobility device components to selectively configure and modulate the at least one joint component; providing within said mobility assistance device a control application to be executed by the control system; providing within said mobility assistance device a plurality of sensors to detect a state of the at least one actuator component and/or the at least one joint component; integrating into said mobility assistance device a functional electrical stimulation (FES) system, wherein the FES system includes an FES stimulator that is embedded within a component of the mobility assistance device; and executing the control application with the control system to perform FES with the FES system in combination with selectively configuring and modulating the at least one joint component.

The FES system includes a plurality of channels for FES, and control methods further include configuring the channels for the stimulation of different muscle groups of a user of the mobility assistance device. The different muscle groups may include a combination of leg muscle groups and torso muscle groups. The channels may be configured to stimulate the different muscle groups in accordance with stance and swing states of muscle groups during a gait of a user of the mobility assistance device.

In exemplary embodiments, the control methods include operating the FES system in accordance with dynamic functional FES control The dynamic functional FES control may include steps of inputting a muscle profile that is specific to a user of the mobility assistance device, and executing the control application in a manner that is timed with a gait of the user of the mobility assistance device to control a level of contribution of user muscles via FES applied to user muscle groups relative to assistance by the mobility assistance device to the user's gait. The control application may be dynamically executed to adjust in real time FES parameters and torque applied by the at least one joint component during the gait of the user. The FES parameters and torque are adjusted automatically to balance the user's muscle contribution to gait relative to assistance provided by the mobility assistance device.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

DETAILED DESCRIPTION

Figure 1:
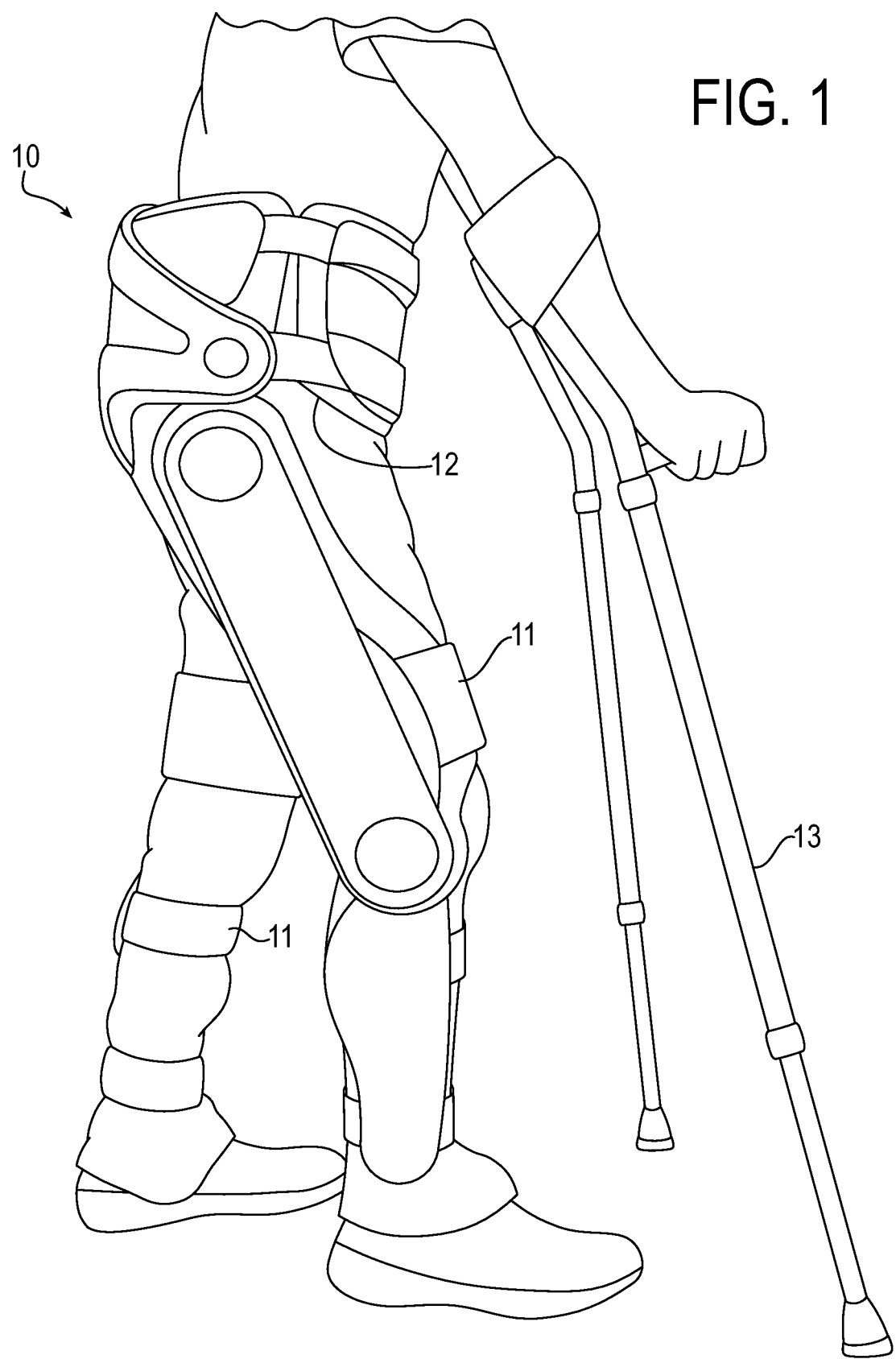
FIG. 1 is a drawing depicting an exemplary exoskeleton device as being worn by a user.

Embodiments of the present invention will now be described with reference to the drawings, wherein like reference numerals are used to refer to like elements throughout. It will be understood that the figures are not necessarily to scale.

For context, FIGS. 1-6 depict various views of an exemplary exoskeleton device that may be used in connection with the integrated FES system and FES control methods of the present invention. A somewhat generalized description of such exoskeleton device is provided here for illustration purposes. A more detailed description of such device may be found in Applicant's International Patent Appl. No. PCT/US2015/023624 filed on Mar. 3, 2015, which is incorporated here in its entirety by reference. It will be appreciated, however, that the described exoskeleton device presents an example usage, and that the integrated FES system and methods of the present invention are not limited to any particular configuration of an exoskeleton device. Variations may be made to the exoskeleton device, while the features of the present invention remain applicable. In addition, the principles of this invention may be applied generally to any suitable mobility assistance device. Such mobility assistance devices include, for example, orthotic devices which aid in mobility for persons without use or limited use of a certain body portion, and prosthetic devices, which essentially provide an electro-mechanical replacement of a body part that is not present such as may be used by an amputee or a person congenitally missing a body portion.

As shown in FIG. 1, an exoskeleton device 10, which also may be referred to in the art as a "wearable robotic device", can be worn by a user. To attach the device to the user, the device 10 can include attachment devices 11 for attachment of the device to the user via belts, loops, straps, or the like. Furthermore, for comfort of the user, the device 10 can include padding 12 disposed along any surface likely to come into contact with the user. The device 10 can be used with a stability aid 13, such as crutches, a walker, or the like.

Figure 2:
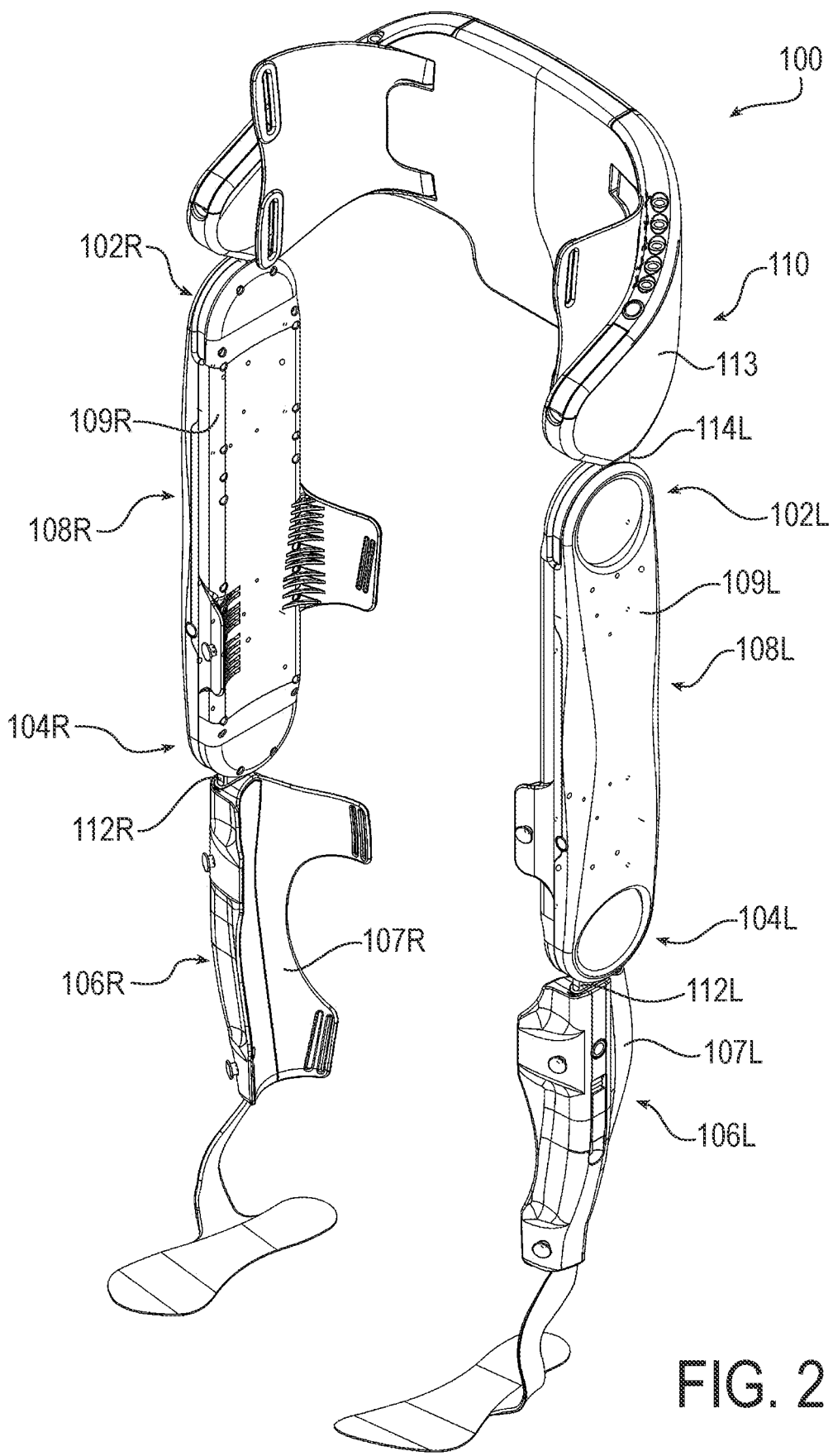
FIG. 2 is a drawing depicting a perspective view of an exemplary exoskeleton device in a standing position.
Figure 3:
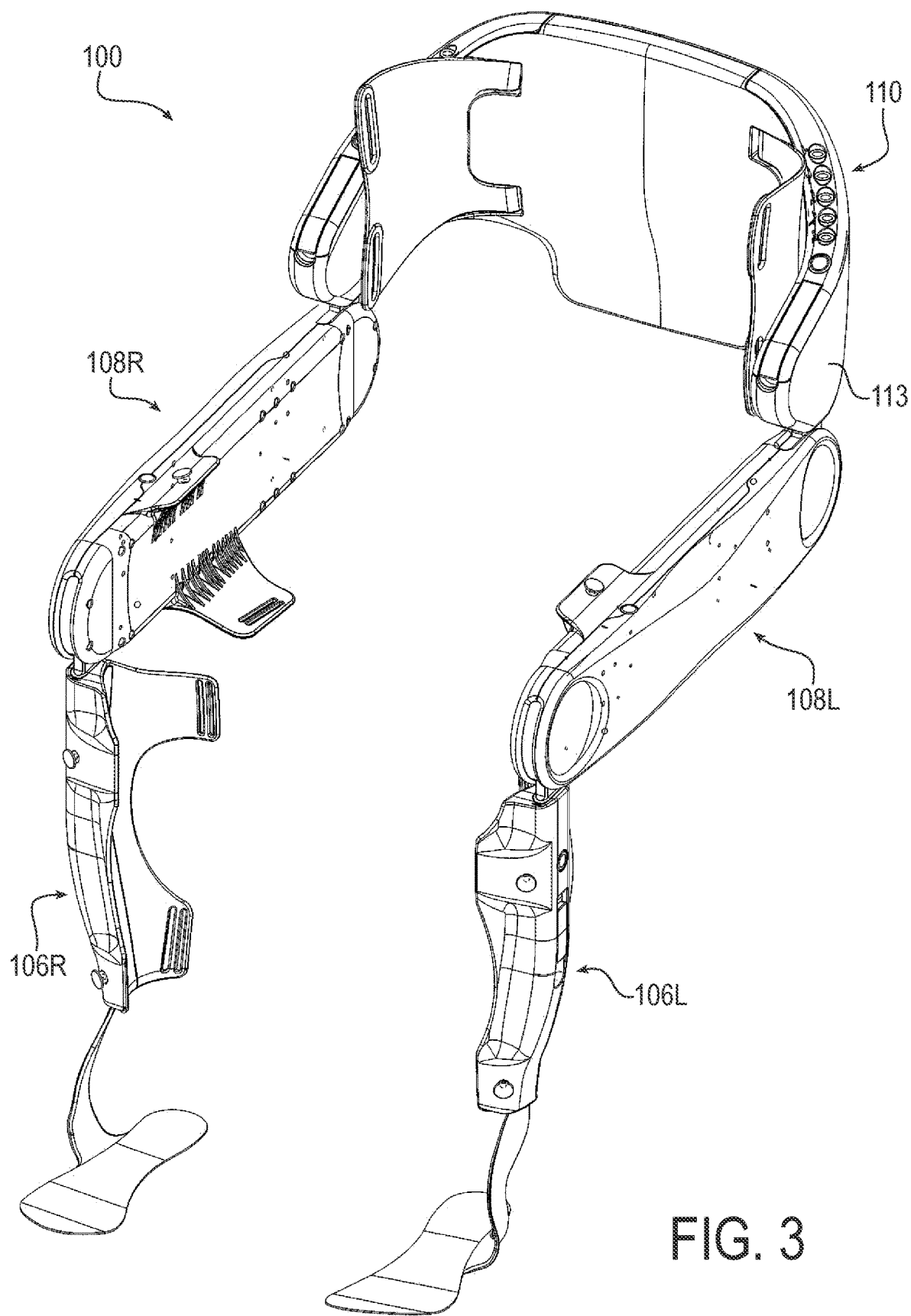
FIG. 3 is a drawing depicting a perspective view of the exemplary exoskeleton device in a seated position.
Figure 4:
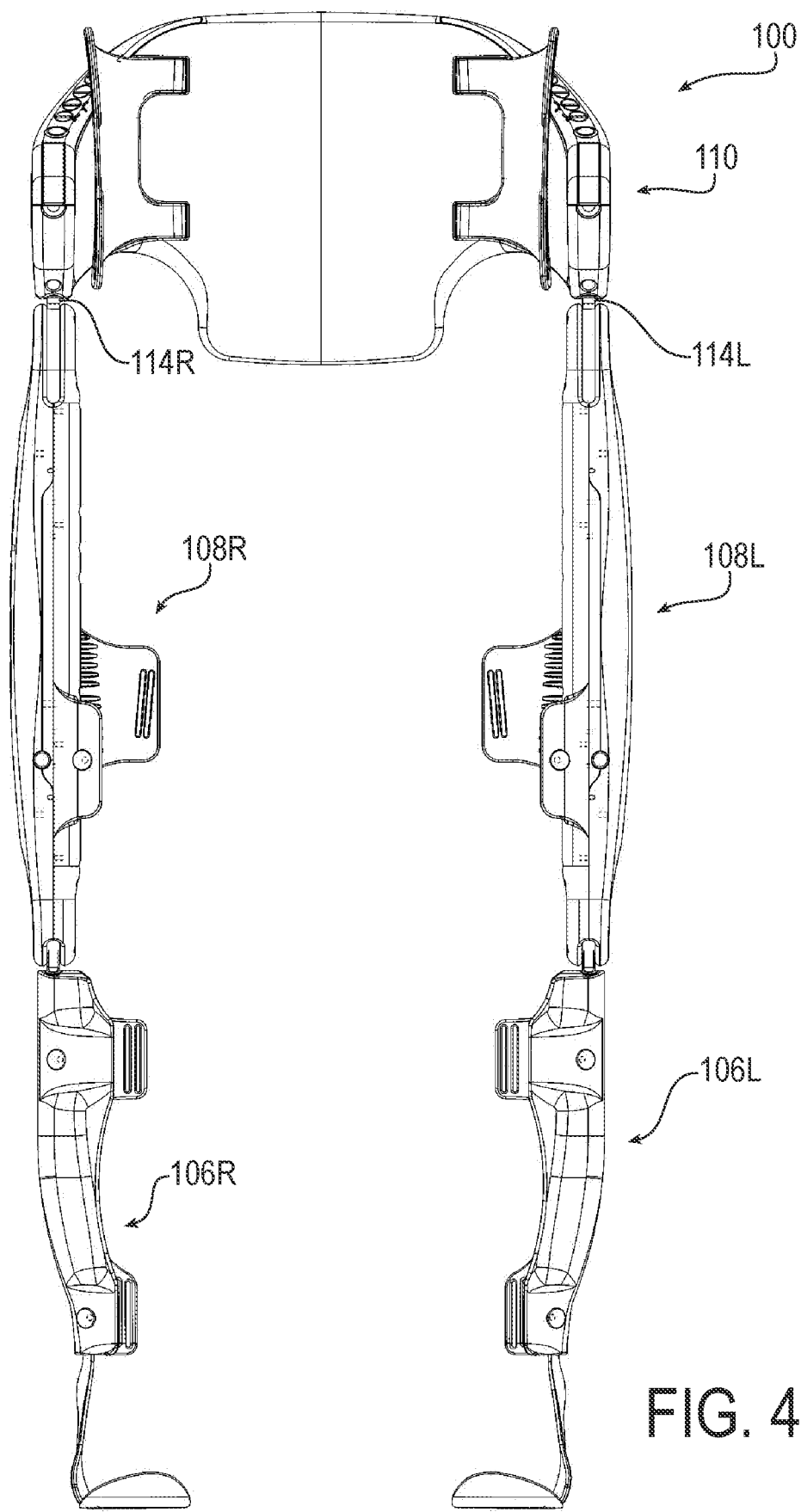
FIG. 4 is a drawing depicting a front view of the exemplary exoskeleton device in a standing position.
Figure 5:
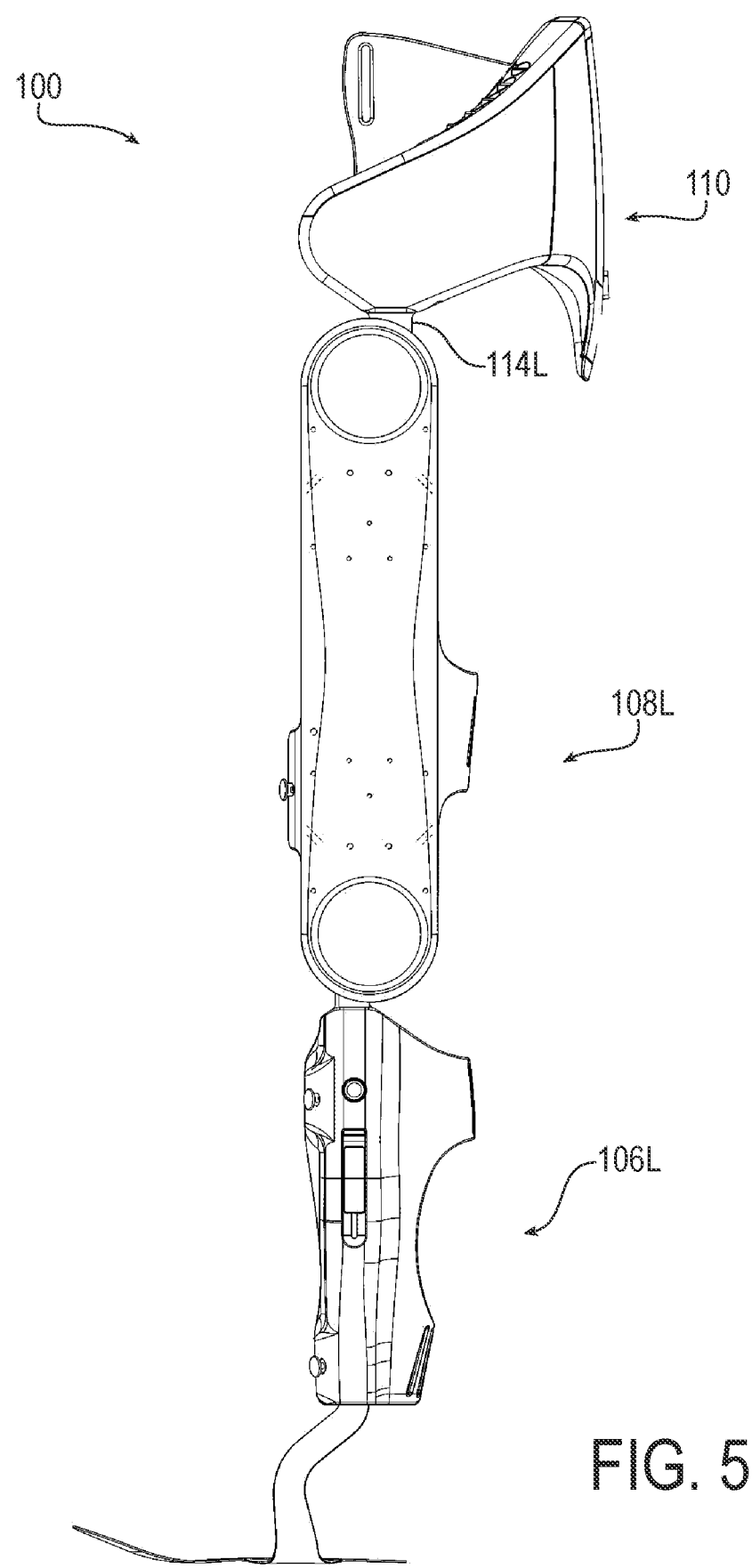
FIG. 5 is a drawing depicting a side view of the exemplary exoskeleton device in a standing position.
Figure 6:
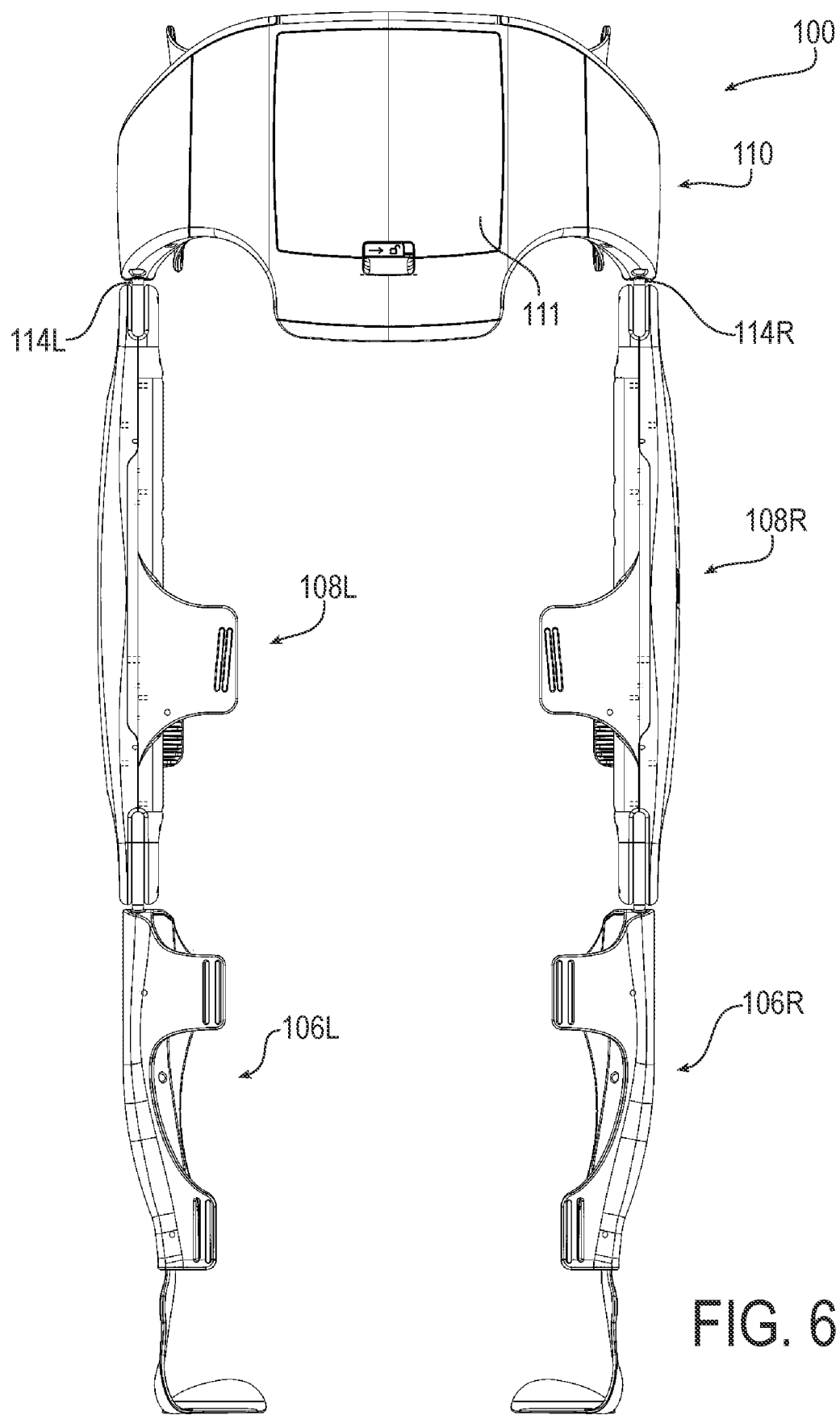
FIG. 6 is a drawing depicting a back view of the exemplary exoskeleton device in a standing position.

An exemplary legged mobility exoskeleton device is illustrated as a powered lower limb orthosis 100 in FIGS. 2-6. Specifically, the orthosis 100 shown in FIGS. 2-6 may incorporate four drive components configured as electromotive devices (for example, electric motors), which impose sagittal plane torques at each knee and hip joint components including (right and left) hip joint components 102R, 102L and knee joint components 104R, 104L. FIG. 2 shows the orthosis 100 in a standing position while FIG. 3 shows the orthosis 100 in a seated position.

As seen in the figures, the orthosis contains five assemblies or modules, although one or more of these modules may be omitted and further modules may be added (for example, arm modules), which are: two lower (right and left) leg assemblies (modules) 106R and 106L, two (left and right) thigh assemblies 108R and 108L, and one hip assembly 110. Each thigh assembly 108R and 108L includes a respective thigh assembly housing 109R and 109L, and link, connector, or coupler 112R and 112L extending from each of the knee joints 104R and 104L and configured for moving in accordance with the operation of the knee joints 104R and 104L to provide sagittal plane torque at the knee joints 104R and 104L.

The connectors 112R and 112L further may be configured for releasably mechanically coupling each of thigh assembly 108R and 108L to respective ones of the lower leg assemblies 106R and 106L. Furthermore, each thigh assembly 108R and 108L also includes a link, connector, or coupler 114R and 114L, respectively, extending from each of the hip joint components 102R and 102L and moving in accordance with the operation of the hip joint components 102R and 102L to provide sagittal plane torque at the knee joint components 104R and 104L. The connectors 114R and 114L further may be configured for releasably mechanically coupling each of thigh assemblies 108R and 108L to the hip assembly 110.

In some embodiments, the various components of device 100 can be dimensioned for the user. However, in other embodiments the components can be configured to accommodate a variety of users. For example, in some embodiments one or more extension elements can be disposed between the lower leg assemblies 106R and 106L and the thigh assemblies 108R and 108L to accommodate users with longer limbs. In other configurations, the lengths of the two lower leg assemblies 106R and 106L, two thigh assemblies 108R and 108L, and one hip assembly 110 can be adjustable. That is, thigh assembly housings 109R, 109L, the lower leg assembly housings 107R and 107L for the lower leg assemblies 106R, 106L, respectively, and the hip assembly housing 113 for the hip assembly 110 can be configured to allow the user or medical professional to adjust the length of these components in the field. For example, these components can include slidable or movable sections that can be held in one or more positions using screws, clips, or any other types of fasteners. In view of the foregoing, the two lower leg assemblies 106R and 106L, two thigh assemblies 108R and 108L, and one hip assembly 110 can form a modular system allowing for one or more of the components of the orthosis 100 to be selectively replaced and for allowing an orthosis to be created for a user without requiring customized components. Such modularity can also greatly facilitate the procedure for donning and doffing the device.

In orthosis 100, each thigh assembly housing 109R, 109L may include substantially all the drive components for operating and driving corresponding ones of the knee joint components 104R, 104L and the hip joint components 102R, 102L. In particular, each of thigh assembly housings 109R, 109L may include drive components configured as two motive devices (e.g., electric motors) which are used to drive the hip and knee joint component articulations. However, the various embodiments are not limited in this regard, and some drive components can be located in the hip assembly 110 and/or the lower leg assemblies 106R, 106L.

A battery 111 for providing power to the orthosis can be located within hip assembly housing 113 and connectors 114R and 114L can also provide means for connecting the battery 111 to any drive components within either of thigh assemblies 108R and 108L. For example, the connectors 114R and 114L can include wires, contacts, or any other types of electrical elements for electrically connecting battery 111 to electrically powered components in thigh assemblies 108R and 108L. In the various embodiments, the placement of battery 111 is not limited to being within hip assembly housing 113. Rather, the battery can be one or more batteries located within any of the assemblies of orthosis 100.

The referenced drive components may incorporate suitable sensors and related internal electronic controller or control devices for use in control of the exoskeleton device. Such internal control devices may operate using the sensory information from the detection of postural cues, by which the internal control device will automatically cause the exoskeleton device to enter generalized modes of operation, such as sitting, standing, walking, variable assist operation, and transitions between these generalized modes or states (e.g., Sit to Stand, Stand to Walk, Walk to Stand, Stand to Sit, etc.) and step transition (e.g., Right Step, Left Step). The internal electronic control devices further may perform fall mitigation and recovery operations for the exoskeleton device, as described for example in Applicant's International Patent Appl. No. PCT/US2016/016319 filed on Feb. 3, 2016, which is incorporated here in its entirety by reference.

The internal electronic control devices and related electronics further may incorporate or include a mobility assistance device communications interface that is configured to transmit and receive signals over an electronic signal interface. In exemplary embodiments, the mobility device communications interface may communicate electronically over a wireless interface by transmitting signals to and receiving signals from a communications interface of an electronic communication device including a control application for controlling the drive components of the mobility device.

To perform such operations, the drive systems and internal control device of the mobility assistance device may employ the use of accelerometers, gyroscopes, inertial measurement, and other sensors to detect and observe the upper leg, hip, and knee orientations, angles, and/or angular velocities. The internal control device may then selectively control the drive components to modulate the joint components, and particularly the knee and hip joint components, to apply torque, implement locked or released states, or otherwise effect positioning or movement of the joint components to control the exoskeleton device for modes operation or for fall mitigation.

To implement the features of the present invention, the exoskeleton device or other mobility device may include a control system having one or more processor devices that are configured to execute program code stored on a non-transitory computer readable medium embodying the control methods associated with the generalized control of the exoskeleton device, including the control operations of the present invention. It will be apparent to a person having ordinary skill in the art of computer programming of electronic devices how to program the electronic control device to operate and carry out logical functions associated with present invention. Accordingly, details as to specific programming code have been left out for the sake of brevity. Also, controller functionality could be carried out via dedicated hardware, firmware, software, or any combinations thereof, without departing from the scope of the invention. As will be understood by one of ordinary skill in the art, therefore, the control system may have various implementations. For example, the control system may be configured as any suitable processor device, such as a programmable circuit, integrated circuit, memory and I/O circuits, an application specific integrated circuit, microcontroller, complex programmable logic device, other programmable circuits, or the like. The control system may also include a non-transitory computer readable medium, such as random access memory (RAM), a read-only memory (ROM), an erasable programmable read-only memory (EPROM or Flash memory), or any other suitable medium. Instructions for performing the methods described below may be stored in the non-transitory computer readable medium and executed by the processor device.

Figure 7:
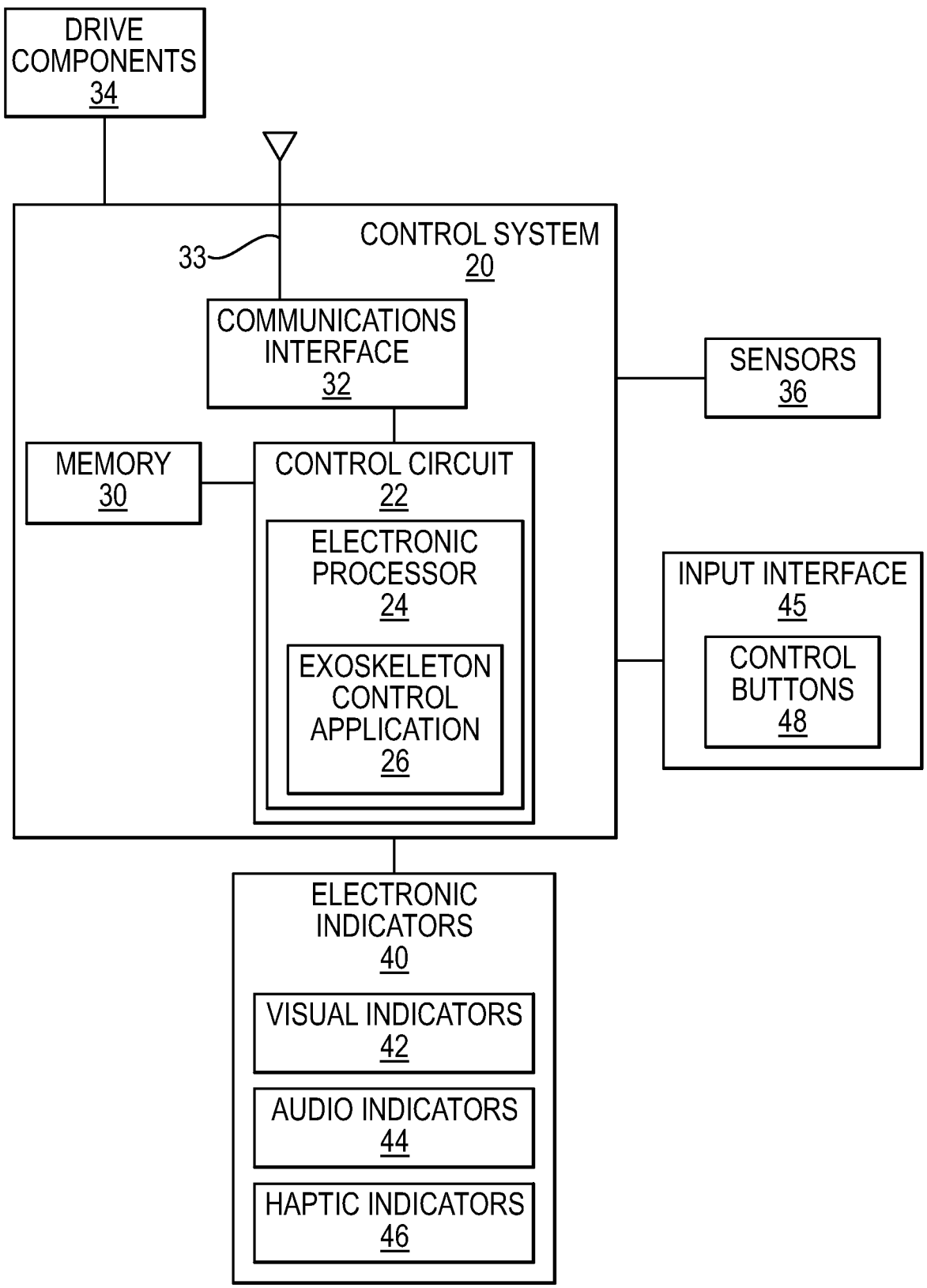
FIG. 7 is a drawing depicting a schematic block diagram of operative portions of an exemplary control system and related electronic components of a mobility assistance device in accordance with embodiments of the present invention.

FIG. 7 is a drawing depicting a schematic block diagram of operative portions of an exemplary control system 20 and related electronic components in accordance with embodiments of the present invention, that is a component of the mobility assistance device such as the exoskeleton device of the previous figures. The control system 20 may include a primary control circuit 22 that is configured to carry out various control operations relating to control of the exoskeleton device. The control circuit 22 may include an electronic processor 24, such as a CPU, microcontroller or microprocessor. Among their functions, to implement the features of the present invention, the control circuit 22 and/or electronic processor 24 may comprise an electronic controller that may execute program code embodied as the exoskeleton control application 26. It will be apparent to a person having ordinary skill in the art of computer programming, and specifically in application programming for electronic and communication devices, how to program the device to operate and carry out logical functions associated with application 26. Accordingly, details as to specific programming code have been left out for the sake of brevity.

The exoskeleton control application 26 may be stored in a non-transitory computer readable medium, such as random access memory (RAM), a read-only memory (ROM), an erasable programmable read-only memory (EPROM or Flash memory), or any other suitable medium. In the example of FIG. 7, the exoskeleton control application 26 is shown as being stored internally within the processing components, but the application also may be stored in an additional memory device such as the memory 30. Instructions for performing the methods described below that are stored in the non-transitory computer readable medium may be executed by the processor components 22 and 24. Also, while the code may be executed by control circuit 22 or processor 24 in accordance with an exemplary embodiment, such controller functionality could also be carried out via dedicated hardware, firmware, software, or combinations thereof, without departing from the scope of the invention.

The control system 20 may constitute internal electronic control devices and related electronics incorporated into one or more of the exoskeleton device components, and typically may be incorporated into one or more of the thigh assembly or hip assembly components of the exoskeleton device. The control system 20 further may include a communications interface 32 for electronic communication with components external to the control system. For example, the communications interface may provide for electronic communication via an antenna 33 with an external mobile communication device, and thus may be configured to transmit and receive signals over an electronic signal interface. In exemplary embodiments, the communications interface may communicate electronically with an external mobile communication device over a wireless interface by transmitting signals to and receiving signals from the drive components for control of the mobility device. A mobile communications device and related control systems and methods are disclosed Applicant's International Patent Appl. No. PCT/US2016/40304 filed on Jun. 30, 2016, which is incorporated here in its entirety by reference.

The control system 20 further may be in electronic communication with both sensory and drive components of the exoskeleton device. The connections may be hard wired connections via internal circuit boards and other wired connections, but wireless communication also may be employed between the control system and/or sensor and drive components. In FIG. 7 the drive components are generally indicated by block 34, and the sensors are generally indicated by block 36. For gathering appropriate sensory information, the sensors 36 may include the use of accelerometers, gyroscopes, inertial measurement, and other sensors to detect and observe the upper leg and torso orientation or angle and angular velocity. Example sensors may include hall effect sensors, magnetic angle sensors, accelerometer sensors, gyroscope sensors, resistance temperature detectors, and others. There also may be one or more redundant sensors that correspond respectively to one or more of the above sensors, and the redundant sensors may provide sensor information when there is a sensor fault detected in a respective sensor.

The control system 20 may then selectively control the drive components 34 to configure and modulate the joint components of the exoskeleton device, and particularly the knee and hip joint components, to apply torque, implement locked or released states, or otherwise effect positioning or movement of the joint components for control of the exoskeleton device for various modes of operation and for fall mitigation.

As described for example in Applicant's referenced previous patent applications, in the described exoskeleton device operation generally is automated based on sensory detections. As an example, to go from sit to stand a user may pull in the legs and lean forward, as any person normally does when getting ready to stand. Upon sensing such a pre-standing position, the exoskeleton drive system would send a haptic feedback signal to the user, such as a vibration indicator, informing the user that a transition to standing will occur. Control of mobility mode of operation (sit, stand, walk, etc.), and transitions between mobility modes, proceeds as warranted. Mode transitions and mode operations, therefore, are operated generally by the sensors reading user postural cues, which are interpreted by the control system that in turn generates control signals to drive operation of the drive components.

The control system 20 further may be in electronic communication with a plurality of electronic indicators 40. In FIG. 7, the electronic indicators are generally indicated by block 40. The electronic indicators may include visual indicators 42 that indicate aspects of device state and operation by lighting. In exemplary embodiments, the lighting may be color-coded lighting in which light emitting diodes (LEDs) are employed as the visual indicators. The electronic indicators further may include audio indicators 44, by which speakers may be employed to provide audio alerts pertaining to aspects of device state and operation. Different sounds may be employed for different types of audio alerts, and may be used in combination with the visual indicators 42 to provide multiple indicator combinations corresponding to information pertaining to different aspects of device state and operation. The electronic indicators further may include haptic indicators 46. The haptic indicators 46 may be configured as vibration generators that provide vibration indications as alerts pertaining to aspects of device state and operation.

The control system 20 further may be in electronic communication with an input interface 45. The input interface may be configured as an electronic control panel on the exoskeleton device that permits user inputs for control of the exoskeleton device. The input interface may include one or more control buttons 48 that may provide a varied array of control options for a user, including a power button for turning on and enabling the exoskeleton device.

The following describes configurations for structural FES integration into an exoskeleton device, such as for example the exoskeleton device illustrated in FIG. 1-6. An FES system integrated into an exoskeleton device provides multiple channels of electrical stimulation without the addition of a hefty external stimulator box or an external communications tether as are typical of conventional configurations. Embodiments of the structural FES integration integrate a ten channel FES stimulator into an exoskeleton device to provide a convenient robotic system capable of providing legged mobility as well as FES, by which a user simultaneously attains the benefits of both FES and the mobility via the exoskeleton device. This pairing is synergistic. Conventional FES systems rely solely on the user's stimulated muscles, and the user therefore may swiftly fatigue when using electrical stimulation alone. The further integration of the FES system into the exoskeleton device permits the exoskeleton device to supplement user effort when stimulation of the user's muscles does not provide adequate power to achieve an appropriate gait. In this manner, control methods may be executed to balance user effort via FES versus device assistance by the exoskeleton joint components as warranted for user strength and performance goals.

As aspect of the invention, therefore, is an integrated FES system that integrates an FES system into a mobility assistance device, such as for example a legged mobility exoskeleton device. In an exemplary embodiment, an integrated FES system includes a component of a mobility assistance device, and an FES system mounted within the component of the mobility assistance device. The FES system includes an FES stimulator that is embedded within the component of the mobility assistance device, and a plurality of FES jacks that are electrically connected to the FES stimulator and are located on the component of the mobility assistance device. The FES jacks are configured to receive a plurality of FES electrodes, and an electrical stimulation output from the FES stimulator is conducted through the FES jacks to the FES electrodes. The component of the mobility assistance device may be a hip component of a legged mobility exoskeleton device including the hip component, a left leg component, and a right leg component. The FES stimulator may be embedded within a back portion of the hip component, and the FES jacks may be located on wing portions of the hip component.

Figure 8:
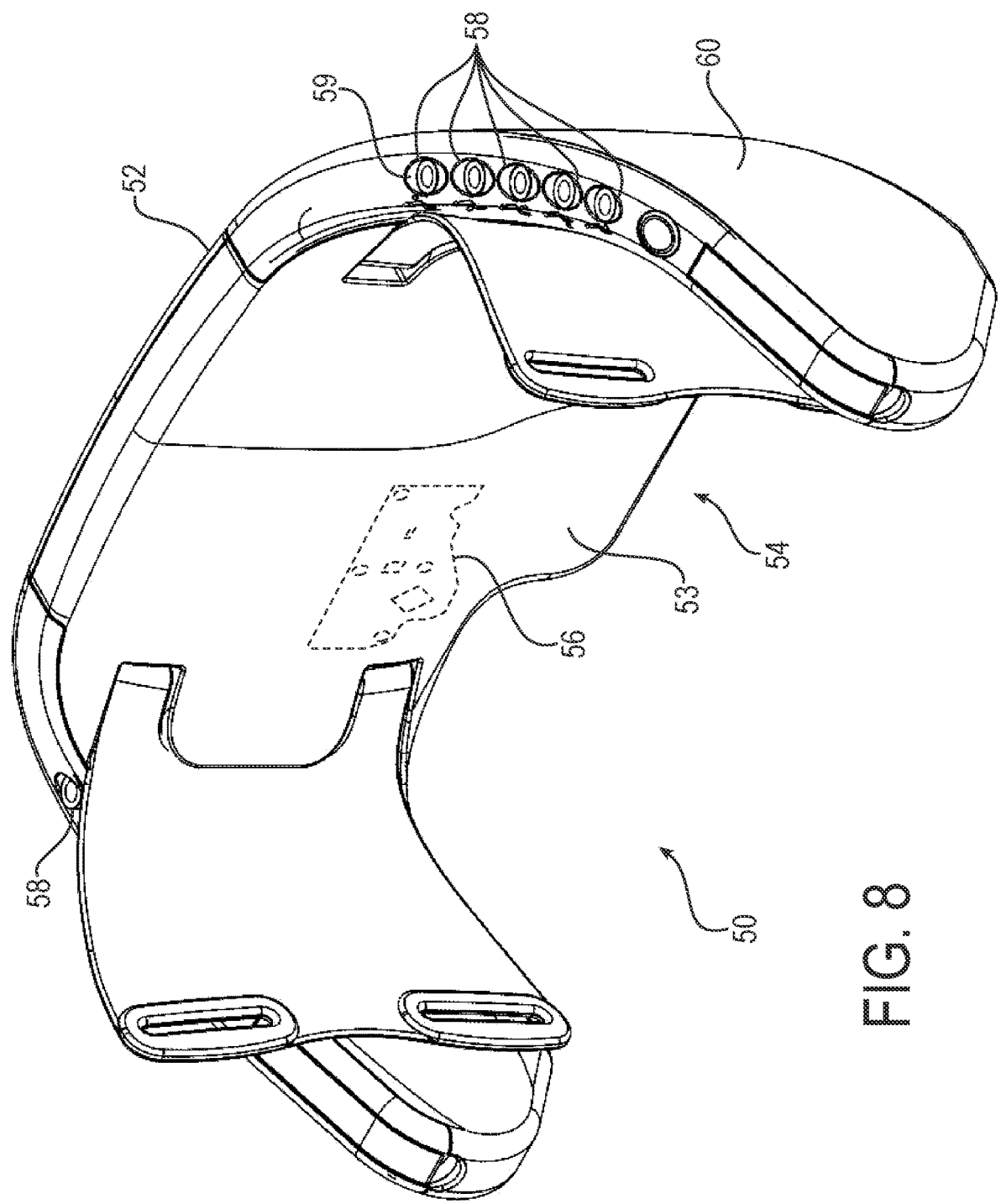
FIG. 8 is a drawing depicting an integrated FES system in accordance with embodiments of the present invention.

FIG. 8 is a drawing depicting an exemplary integrated FES system 50. The integrated FES system 50 includes a component of a mobility assistance device, such as for example a hip component 52 of an exoskeleton device, combined with an FES system 54 that is mounted within the component of the mobility assistance device. In exemplary embodiments, the FES system 54 includes an FES stimulator 56 that is embedded within the component of the mobility assistance device, and a plurality of FES jacks 58 that are electrically connected to the FES stimulator and are located on the component of the mobility assistance device. As further detailed below, the FES jacks 58 are configured to receive a plurality of FES electrodes, and an electrical stimulation output from the FES stimulator 56 is conducted through the FES jacks 58 to the FES electrodes.

In exemplary embodiments, the FES stimulator 56 is configured as a printed circuit board (PCB) that is embedded within a cavity defined by a back portion 53 of the hip component 52. The FES jacks 58 are located on wing portions 60 of the hip component 52. In the illustrated embodiment as an example, there are ten FES jacks corresponding to ten respective channels for potential electrical stimulation output from the FES stimulator. A first portion of the FES jacks (e.g., five FES jacks) may be located on a left wing of the hip component, and a second portion of the FES jacks (e.g., another five FES jacks) may be located on a right wing of the hip component. The hip component 52 is sized and shaped in a manner that lends itself to easy incorporation of the FES system 54, and the various embodiments are described principally in connection with incorporating the FES system into the hip component. It will be appreciated, however, that the integrated FES system 50 is not limited to such a configuration. Any suitable component of the exoskeleton device or comparable mobility assistance device, such as for example the thigh components of an exoskeleton device, alternatively may be provided with the integrated FES stimulator and FES jacks in comparable fashion.

Figure 9:
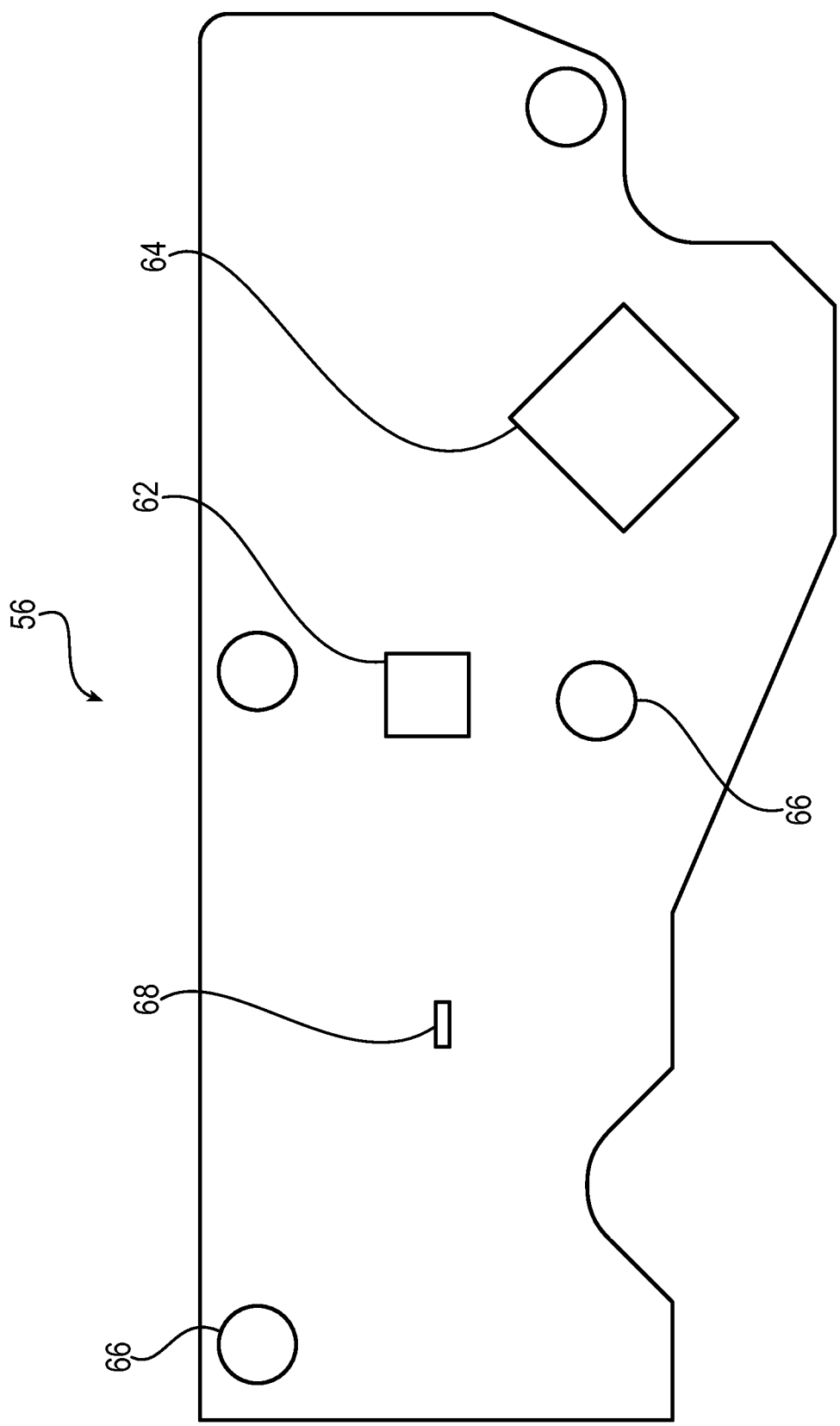
FIG. 9 is a drawing depicting an exemplary PCB FES stimulator for use in the integrated FES system of FIG. 8 in accordance with embodiments of the present invention.

FIG. 9 is a drawing depicting an exemplary PCB FES stimulator 56. In exemplary embodiments, the PCB FES stimulator 56 includes a microprocessor 62 that controls the electrical stimulation output from the FES stimulator, and an electrical transformer 64 that modifies the electrical stimulation output to make the electrical stimulation output suitable for stimulation. The FES stimulator 56 may be powered by the battery that powers the exoskeleton device, or may have its own power source that can be powered or charged by induction. The FES stimulator 56 is mounted in a cavity in the hip component of the exoskeleton device, as referenced above, and the mounting is performed via dedicated attachment points 66. The attachment points 66 may be configured, for example, as openings for grommets and screws, so that the FES stimulator 56 is fully contained within the hip component 52. The FES stimulator 56 further includes a communications port 68 configured to communicate with electronics of the mobility assistance device to synchronize the electrical stimulation output with actions of at least one component of the mobility assistance device, as further detailed below. This permits the exoskeleton device's control system (see FIG. 7) to provide information to synchronize electrical stimulation with exoskeleton actions (e.g. stepping or standing up). Settings and other information from the referenced mobile application for controlling the exoskeleton device also can be received via wireless communication by the FES stimulator 56, or received by the exoskeleton control system and transferred to the FES stimulator via internal wiring.

Figure 10:
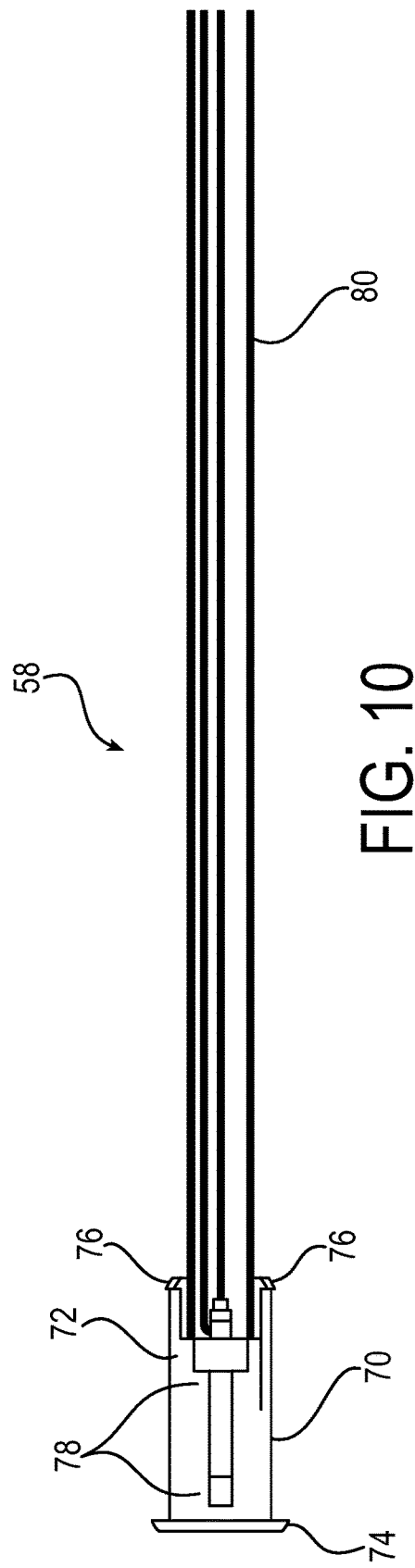
FIG. 10 is a drawing depicting an exemplary FES jack in accordance with embodiments of the present invention.

FIG. 10 is a drawing depicting an exemplary FES jack 58. In exemplary embodiments, the FES jacks 58 each includes a cup 70 that contains a light emitting device 72. For example, the cup 70 may be a plastic cup that is over-molded about a light emitting diode (LED) or other comparable light emitting device. For incorporating the FES jack 58 into the hip component, the FES jack 58 may include a lip 74 to provide a secure fit interaction with the component of the mobility device, such as to fix the jack in place in a respective open socket 59 located in the hip component 52 (see also FIG. 8.) The FES jacks 58 further may include flexible tabs 76 that are shaped to provide a secure connection, such as an interference fit, between the FES jacks and the FES electrodes to maintain the FES electrodes in place within the FES jacks. Each FES jack 58 further includes electrical contacts 78 that conduct the electrical stimulation output from the FES stimulator 56 to an FES electrode that is plugged into or otherwise connected to the FES jack. In a wired configuration, electrical connections such as wiring 80 runs internally within the hip component 52 between the electrical contacts 78 and the FES stimulator 56. In this manner, an electrode that is connected into the FES jack 58 becomes electrically connected to the FES stimulator 56. By running the electrical wiring 80 internally within the hip component 52 or other component of the mobility assistance device, external wiring is minimized.

Figure 11:
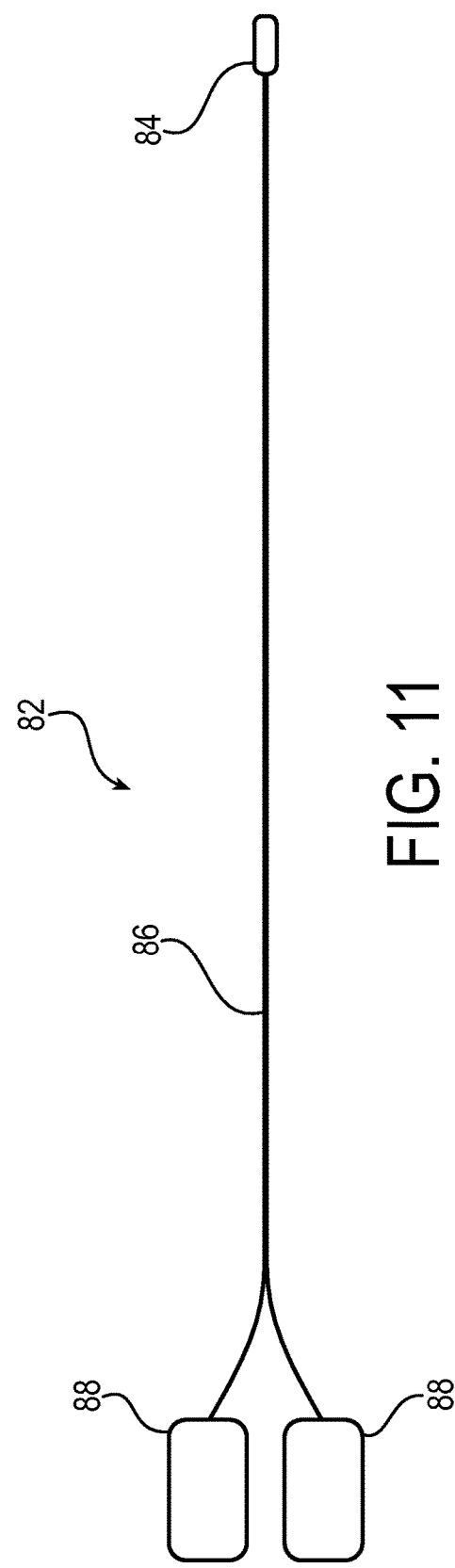
FIG. 11 is a drawing depicting an exemplary FES electrode that may be used with the integrated FES system of the present invention.

FIG. 11 is a drawing depicting an exemplary FES electrode 82 that may be used with the integrated FES system 50. In conventional FES systems, surface electrodes are normally designed with a short (e.g., approximately 2") lead wire that terminates in a standardized plastic connector for connection into an external FES stimulator box so that the electrode can be placed anywhere on the body and connected to any FES system with matching connectors. Because exoskeletons place a robotic component against the user's skin, it is possible for standard plastic connectors to cause serious skin abrasions if they are placed between the skin and the exoskeleton. In a preferred electrode design for use with the integrated FES system 50, the electrode 82 includes a connector 84 that plugs directly into the FES jack 58. As referenced above, the tabs 76 of the FES jacks provide for a secure, interference connection of the FES electrode to the FES jack.

When connected, the FES electrode connector 84 forms an electrical connection with the electrical contacts 78 of the FES jack 58, which ultimately in turn provides an electrical connection from the FES stimulator 56 to the electrode 82. With such configuration, the electrode connector 84 plugs directly into the FES jack 58 such that only flexible wires may be present between the exoskeleton device and the user's skin, which reduces the potential for skin irritation. The electrode 82 further includes lead wiring 86 that runs from the electrode connector 84 to electrode pads 88, which may be disposable. Such configuration includes a significantly longer portion of lead wiring 86 to be attached directly to the disposable electrode pads 88 as compared to conventional configurations. This permits the electrodes to be distributed as a pair of electrode pads 88 that is wired together as shown in FIG. 11, thereby minimizing the likelihood that electrodes would be accidentally connected to the wrong lead wiring which is a common safety hazard of conventional FES configurations.

In alternative embodiment, the integrated FES system is wireless. In the wireless configuration, the FES stimulator is embedded within the component of the mobility assistance device, and is configured to wirelessly transmit a control signal for applying an electrical stimulation output to a plurality of FES electrodes. The wireless FES stimulator may be embedded within a back portion of the hip component of an exoskeleton device. The FES system may include a centralized stimulator and power hub that receives the control signal from the FES stimulator and outputs the electrical stimulation output to multiple networked FES electrodes, or the FES stimulator may be configured to transmit the control signal to multiple non-networked distributed FES electrodes including embedded power and communication components within each electrode.

Figure 12:
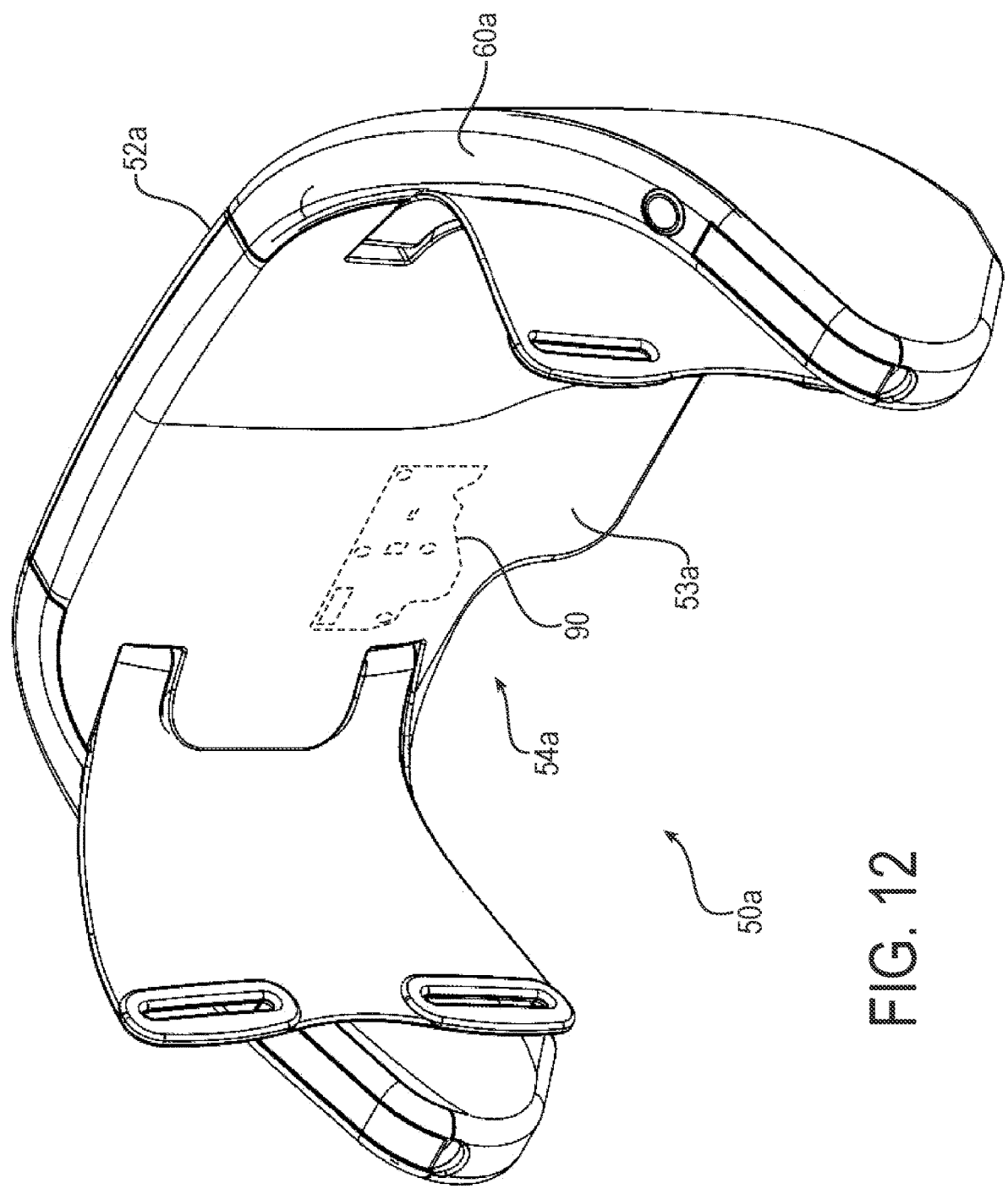
FIG. 12 is a drawing depicting a wireless integrated FES system in accordance with embodiments of the present invention.
Figure 13:
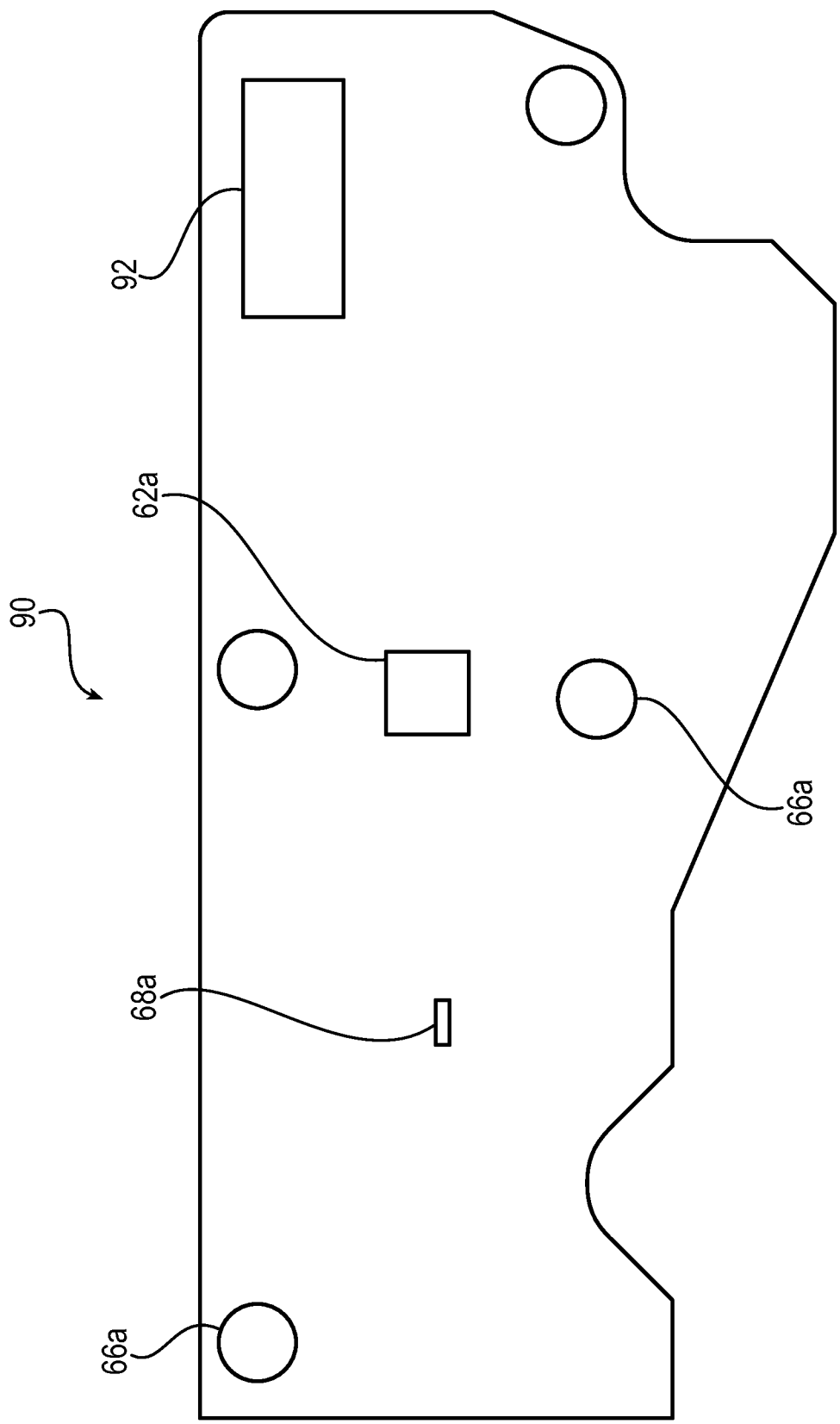
FIG. 13 is a drawing depicting an exemplary PCB FES stimulator for use in the wireless integrated FES system of FIG. 12 in accordance with embodiments of the present invention.

FIGS. 12 and 13 illustrate an exemplary configuration of the alternative embodiment in which a wireless integrated FES system 50a is provided in accordance with embodiments of the present invention. Similarly as in the previous embodiment, as shown in FIG. 12, the integrated FES system 50a includes a component of a mobility assistance device, such as a hip component 52a of an exoskeleton device, into which there is integrated an FES system 54a. In exemplary embodiments, the FES system 54a includes an FES stimulator 90. The FES stimulator 90, comparably as in the previous embodiment, may be configured as a printed circuit board (PCB) that is embedded within a cavity defined by a back portion 53a of the hip component 52a. Because the integrated FES system 54a of this embodiment is wireless, the FES jacks utilized in the previous embodiment are eliminated, and wing portions 60a of the hip component 52a are configured as solid pieces or having a solid covering. Again, the hip component 52a is sized and shaped in a manner that lends itself to easy incorporation of the FES system 54a, but this is a non-limiting example. Any suitable component of the exoskeleton device or comparable mobility assistance device, such as for example the thigh components of an exoskeleton device, alternatively may be provided with the integrated FES stimulator in comparable fashion.

FIG. 13 is a drawing depicting an exemplary PCB FES stimulator PCB 90 in accordance with wireless embodiments of the present invention. Similar to the previous embodiment, the PCB FES stimulator 90 includes a microprocessor 62a that controls transmission of a control signal for the electrical stimulation output from the FES stimulator. The FES stimulator 90 may be comparably mounted in the cavity in the hip component of the exoskeleton device via dedicated attachment points 66a, which again may be configured, for example, as openings for grommets and screws, so that the FES stimulator 90 is fully contained with the hip piece 52a. The FES stimulator 90 further includes a communications port 68a so that the exoskeleton's electronics can provide information to synchronize electrical stimulation with exoskeleton actions and settings, and exchange other information with a mobile application for controlling the exoskeleton device and/or from the exoskeleton device control system.

The FES stimulator 90 includes a wireless transmitter 92 that wirelessly transmits the control signal for the electrical stimulation output. More particularly, the wireless transmitter may communicate with a centralized stimulator component with a power hub that receives the control signal from the FES stimulator and outputs the electrical stimulation output to networked FES electrodes in electrical or signal communication with the centralized stimulator component. In another embodiment, the FES stimulator is configured to transmit the control signal to a system of non-networked distributed FES electrodes including embedded power and communication components contained within each of the FES electrodes. Accordingly, for the wireless embodiment of the FES stimulator 90, the transformer element of the previous embodiment is eliminated, as the components inducing the electrical current would be distributed within the electrodes themselves. The various components in the wireless embodiments may be powered or charged via induction.

Figure 14:
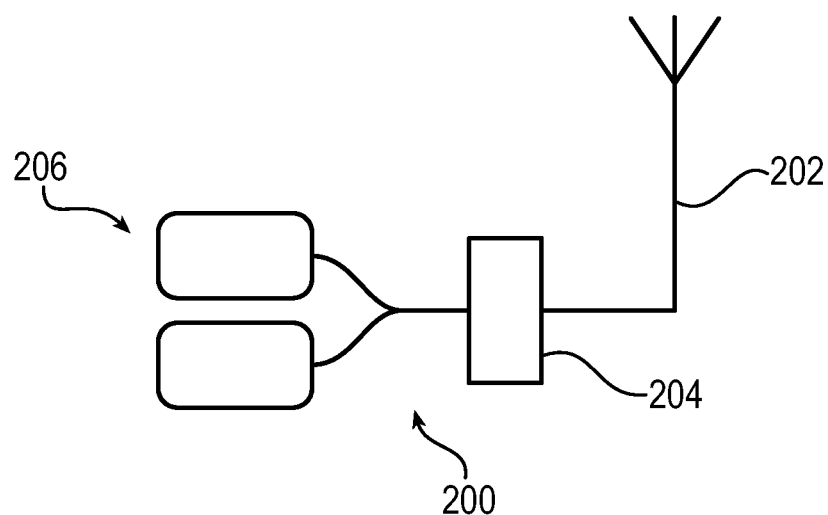
FIG. 14 is a drawing depicting an exemplary configuration of a distributed system of components for a wireless FES integration in an exoskeleton device, in accordance with embodiments of the present invention.
Figure 15:
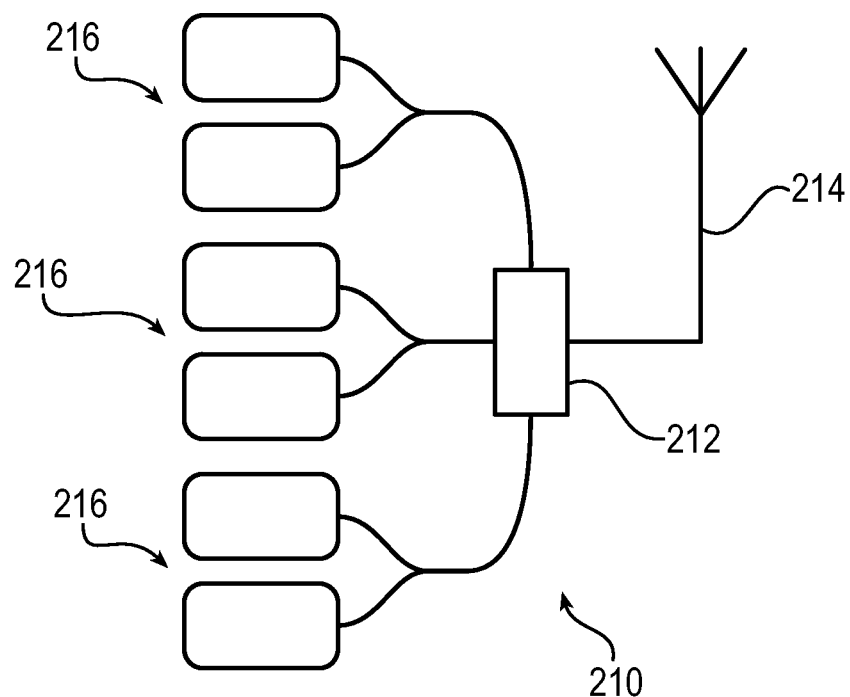
FIG. 15 is a drawing depicting another exemplary configuration of a distributed system of components for a wireless FES integration in an exoskeleton device, in accordance with embodiments of the present invention.

As referenced above, wireless FES in an exoskeleton device may be achieved using either networked electrodes with a centralized stimulator and power hub, or using non-networked, distributed electrodes. In the wireless configuration, numerous individual systems of the FES integration are distributed to various areas of the body to be stimulated. FIGS. 14 and 15 are drawings that illustrate exemplary configurations of the distributed systems for the wireless FES integration in an exoskeleton device. In a first exemplary embodiment shown in FIG. 14, for each targeted muscle group, a distributed unit 200 includes an antenna 202, power supply and stimulation electronics 204, and an electrode 206. A distributed unit 200 is placed near a respective target muscle group, so multiple distributed units 200 are provided for stimulation of the different muscle groups. FIG. 15 shows another exemplary embodiment of a distributed system 210 for the wireless FES integration in an exoskeleton device. In the embodiment of FIG. 15, a distributed system 210 includes a centralized electronics package with power supply 212 that could selectively stimulate one of several electrode pairs in response to incoming information received wirelessly via the antenna 214.

For operation, the wireless transmitter 92 generates a wireless signal to indicate when the FES electrodes in the distributed systems should stimulate. In particular, the wireless transmitter 92 is configured to wirelessly transmit a control signal generated by the FES stimulator 90 for applying an electrical stimulation output to a plurality of FES electrodes, received via the antennas as depicted in FIGS. 14 and 15.

As referenced above in the background section, there are significant advantages to using advanced implantable electrodes that can be placed at the internal location of the target stimulation. However, conventional FES systems using implantable electrodes previously have not been integrated into a powered exoskeleton device as disclosed herein. By integrating wireless FES using implantable electrodes with a powered exoskeleton device, deficiencies of conventional systems are eliminated while improving the capabilities of the powered exoskeleton device. Because of the highly configurable capabilities of an exoskeleton device with wireless communications built in, the powered exoskeleton system easily integrates communications for control methods with power delivery methods into the robotic exoskeleton device, permitting the communications and power systems to be intelligently coupled. This expands the capabilities of the exoskeleton device even above configurations that use surface electrodes applied to the skin, expanding the options for which muscles could be stimulated, and improving the quality of stimulation.

The integrated FES system 50/50a operates as follows. Generally, an aspect of the invention is a control method of controlling a mobility assistance device having a plurality of mobility assistance device components including at least one actuator component that drives at least one joint component.

In exemplary embodiments, the control method comprises the steps of: providing said mobility assistance device, said mobility assistance device further including a control system for controlling operation of the mobility assistance device components to selectively configure and modulate the at least one joint component; providing within said mobility assistance device a control application to be executed by the control system; providing within said mobility assistance device a plurality of sensors to detect a state of the at least one actuator component and/or the at least one joint component; integrating into said mobility assistance device a functional electrical stimulation (FES) system, wherein the FES system includes an FES stimulator that is embedded within a component of the mobility assistance device; and executing the control application with the control system to perform FES with the FES system in combination with selectively configuring and modulating the at least one joint component.

In exemplary embodiments, the control methods include operating the FES system in accordance with dynamic functional FES control The dynamic functional FES control may include steps of inputting a muscle profile that is specific to a user of the mobility assistance device, and executing the control application in a manner that is timed with a gait of the user of the mobility assistance device to control a level of contribution of user muscles via FES applied to user muscle groups relative to assistance by the mobility assistance device to the user's gait. The control application may be dynamically executed to adjust in real time FES parameters and torque applied by the at least one joint component during the gait of the user. The FES parameters and torque are adjusted automatically to balance the user's muscle contribution to gait relative to assistance provided by the mobility assistance device.

Generally, the FES system includes a plurality of channels for FES, and control methods further include configuring the channels for the stimulation of different muscle groups of a user of the mobility assistance device. The different muscle groups may include a combination of leg muscle groups and torso muscle groups. The channels may be configured to stimulate the different muscle groups in accordance with stance and swing states of muscle groups during a gait of a user of the mobility assistance device.

In a preferred embodiment illustrated in FIG. 8, there are ten FES jacks 58 that respectively can receive ten electrodes 82, corresponding to ten dedicated channels of stimulation. Alternatively to the wired jacks of FES system 50, ten wireless channels are provided by the FES system 50a. Each channel may be associated with stimulation of a particular muscle group as is known in the art. The channels in turn may be grouped in various combinations to derive different muscle stimulation profiles. Generally, the ten channels can achieve up to sixteen different muscle profiles. Certain muscles, such as the quadriceps for example, behave differently in stance versus swing portions of the gait, which results in different muscle profiles relating to stance and swing. Accordingly, different muscle profiles corresponding to stance versus swing states for a given muscle or groups of muscles are achieved by varying the stimulation at the same physical location(s). In this manner, only the referenced ten channels are needed to achieve up to sixteen different muscle profiles as different stimulations for stance and swing may be applied to the same location.

An exemplary configuration would incorporate different FES channels respectively to stimulate the quadricep muscles, hamstring muscles, gastrocnemius muscles (calf muscles), tibialis anterior muscles, and gluteus maximus muscles. For trunk support that enhances usage of the exoskeleton device, a channel also may be configured for trunk stimulation. As alternatives to some of the channels above, for additional support in the torso region, channels may be configured for stimulation of the abs and/or back muscles. Furthermore, channels may be configured relative to stance or swing states as appropriate for muscle groups that behave differently in stance versus swing portions of the gait, which again permits the ten channels to stimulate up to sixteen muscle groups. In an exemplary embodiment, twelve muscle groups are directed to physical muscle control, with the additional four muscle group channels being related or directed to phase control to enhance the stimulation effects.

The systems and methods provide for fully configurable muscle group channels. Users can enable or disable each of the ten provided channels as desired. Any of the muscle groups may be selected for use on any channel. The stimulation profile, including pulse width, pulse amplitude, and/or pulse frequency, may be independently adjusted for each of the ten channels. The channels may be assigned and controlled using the mobile application for control of the exoskeleton device, which is modified to permit specific FES control including, for example, enabling and disabling certain channels, muscle group selection and configuration, and various additional FES settings adjustments. The FES control, therefore, can be performed wirelessly via such a mobile application running on a mobile device such as smartphone, tablet computer, laptop computer, or comparable.

Specific muscle profiles and the related stimulation parameters are user specific and derived by the clinician for each user as is known in the art for FES systems. The user specific information can then be programmed into the exoskeleton control system 20 as part of the exoskeleton control application 26 referenced in FIG. 7. FES stimulation may be applied in a manner timed with the gait for one or both of mobility assistance and therapy. For example, FES stimulation may be increased to stimulate the user's muscles timed with suitable portions of the gait to increase the contribution of user effort to mobility, with the torque output of the device actuators of the exoskeleton joint components being reduced by the control system 20 to decrease mobility assistance provided by the exoskeleton device. Such operation can improve user muscle strength and performance with the exoskeleton device. As the user becomes fatigued due to the FES stimulation and muscle usage, the control system 20 may operate to reverse the relative contributions of the user's muscles and the exoskeleton joint components to the gait, i.e., FES stimulation may be decreased to decrease the contribution of user effort to mobility, with the torque output of the device joint components being increased by the control system 20 so that the exoskeleton device provides more mobility assistance. In this manner, control methods may be executed to balance user effort versus device assistance as warranted for user strength and performance goals. The integrated FES system 50/50a, therefore, provides a synergistic benefit by which the user simultaneously experiences the benefits of both FES and the use of the exoskeleton device.

In accordance with such features, the present invention incudes dynamic functional FES control, by which adjustments to the FES parameters can be made in real time as the user continues to walk, permitting clinicians or other users to immediately alter parameters in response to observed behavior or data reported via the mobile application. As part of the dynamic functional FES control, automatic adjustment of stimulation is performed. The FES control applies and alters the timing of when FES is provided to ensure that the user's muscles contribute to gait. For each muscle group, the FES system selects an appropriate window for stimulation during the gait cycle. This window is expanded and contracted as necessary during an over-ground gait when the speed of the exoskeleton device changes. This adjustment is performed automatically, and does not require any intervention on the part of the user or clinical helper. With this enhanced timing of FES relative to the user gait as measured by the performance of the exoskeleton device, as referenced above the control methods may be executed to balance user effort via FES versus device assistance by the exoskeleton joint components as warranted for user strength and performance goals.

With the dynamic functional FES control, back-drivable system optimization may be performed. The dynamic functional FES control optimizes performance particularly in use of a back-drivable exoskeleton device, i.e., an exoskeleton device in which application of torque to the motor output by the user's muscles results in movement of the motor output. Optimization occurs in that the dynamic functional FES control works with both the user's muscles and the exoskeleton device's motor power to produce movement. In a back-drivable exoskeleton device, the FES is capable of reducing motor torques and instead permitting the user's muscles to provide a significant portion of the power required for movement, which can be varied as either part of the device settings, or in real-time during use as changes in muscle performance as may occur due to muscle fatigue.

Other exemplary control features, without limitation, may include the following. The control methods may include executing the control application to perform a wireless test function whereby FES is provided to a selected muscle group while the user is not walking. The wireless test function provides a stimulus to a selected muscle group when the user is not actively walking. The wireless test function may be embodied in the mobile control application located on the associated mobile device, by which the control application wirelessly transmits the signal from the mobile device to perform a test which is then received by the exoskeleton device, transmitted to the FES stimulator board, and used to output a test pulse on the selected channel. The test pulse uses identical parameters to those that will be used during gait and is intended to provide users with an example of the muscle contraction that will be produced during normal operation. With such a feature, a user can be exposed to stimulation outside of the efforts of actual gait with the exoskeleton device. Users therefore, can be made more comfortable with or accustomed to the FES system in preparation for actual use.

The control methods further may include executing the control application to terminate FES with a detection of a connection loss to FES electrodes. With this feature FES enable/disable and setting adjustments are performed via the wireless mobile application comparably as above, which can potentially electrically disconnect the system from outputting stimulation pulses when the system is exposed to significant interference. In this scenario, the control system detects the disconnection event and permits the user to disable FES via an alternative means, i.e. by pressing a button on the exoskeleton device. FES function resumes when the button is pressed again. This control method can prevent unnecessary or adverse stimulation to the user. For example, if one or more FES electrodes becomes disconnected, stimulation may become more concentrated in the FES electrodes that remain connected. This issue is prevented by terminating FES upon detection of a connection loss to one or more FES electrodes.

The control methods further may include executing the control application to perform a warm-up mode comprising cycling through stimulating muscle groups with the FES system prior to beginning a gait with the exoskeleton device. Some users of FES systems experience muscle spasms, which manifest as strong, undesired muscle contractions, which may occur particularly on start-up of the FES stimulation. Application of stimulation to muscles with spasms often acts to reduce the intensity of the spasm. To account for the potential for spasms, the control system is capable of performing a warm-up routine, prior to beginning walking with the exoskeleton device, which cycles through stimulating muscles without exoskeletal stepping to reduce spasms. Once the warm-up routine has operated to eliminate or at least minimize spasms, ordinary operation of the exoskeleton device with FES control proceeds.

The control methods further may include executing the control application to generate a continuous-stimulation profile for muscle groups associated with torso region stability, and applying FES in accordance with the continuous-stimulation profile. For this feature, the control system can operate to generate a continuous-stimulation profile for muscle groups associated with upper-body stability in the torso region, including for example the trunk, abs, and/or back muscles. Constant stimulation of these muscles produces muscle tone which acts to stabilize the torso, which allows the user to more easily manage the exoskeleton device by enhancing the capabilities of the user achieve postural cues with less effort. Device mode transitions, such as for example sit-to-stand, stand-to-step, and the like are made easier, and additional torso support is provided to enhance the smoothness of the stepping action during gait.

The control methods further may include executing the control application to perform muscle contribution calculations including recording measurements of relative contributions of user muscle groups as stimulated by FES versus assistance by the mobility assistance device to gait. The muscle contribution calculations particularly may be associated with the dynamic functional FES control described above. For this feature, while the FES system is operating, calculations can be made as to how the muscles are working in response to FES, including recording measurements of relative contributions of user muscle as stimulated by FES versus assistance by the exoskeleton device to gait. From this data, adjustments can be made to the FES system operation and exoskeleton joint control to optimize user strength and achieving performance goals based on the muscle contribution calculations.

Referring again back to FIG. 7, the FES stimulation methods of the present invention may be performed by the control system 20, for example via the processor components control circuit 22 and/or processor 24, executing the program code embodying the exoskeleton control application 26 stored on a non-transitory computer readable medium. In general, therefore, aspects of the invention are directed to enhanced methods of controlling a mobility assistance device having a plurality of mobility device components including at least one actuator component that drives at least one joint component, as well as a plurality of sensors to detect a state of the at least actuator component and joint component. The control methods further include performing dynamic functional FES control by providing FES stimulation timed with joint component operation to provide a predetermined balance of user effort by FES stimulation, versus device mobility assistance by operation of the joint component(s), as warranted for user strength and performance goals.

The integrated FES system 50/50a may be operated using the referenced ten channels on a regular basis. A common ten-channel usage for bilateral impairment is to employ eight channels for limb stimulation and two channels for trunk muscle stimulation for additional trunk control and support. The ten channels may be configured to stimulate in various combinations for other suitable muscle profiles, and less than ten channels also may be used depending upon the user and the performance goals or parameters. Four, six, and eight channel combinations for different muscle stimulation protocols commonly may be employed, and as referenced above, considering both stance and stepping states, the ten channels may be configured to achieve up to sixteen muscle profiles.

In exemplary embodiments, the mobility assistance device includes a plurality of indicators respectively corresponding to the plurality of channels for FES, and the control method further includes controlling the indicators to provide different outputs relating to the corresponding channels for FES and related electrodes. For example, as also referenced above, each FES jack 58 in the wired configuration includes a light emitting device 72, such as an LED. The LEDs may light up in different patterns or ways to provide different indications relating to the corresponding FES jack and the related electrode. For example, the LED for a given FES jack may light as a solid light when the corresponding channel is being stimulated. The LED for a given jack may blink at a first rate (e.g., a relatively slow rate) when settings are being modified for that channel or when performing a test function for that channel. The LED for a given jack may blink at a second rate (e.g., relatively rapidly as compared to the first rate) when the FES stimulator attempts to stimulate but no complete circuit is detected, such as when an electrode pad has come loose, or the electrode has become unplugged from the FES jack. An indication of circuit insufficiency provides a safety feature to prevent skin irritation, or even burns, due to over-stimulation. When the stimulation current for one jack becomes disrupted, the current can be distributed to other remaining jacks resulting in a more concentrated stimulation via the jacks that remain connected. The LEDs can alert the user to such a deficiency to avoid skin damage. It will be appreciated that the LED operation described in this paragraph is a non-limiting example. Any suitable parameters of light emission, differing in color, timing, duration, occurrence, and the like may be programmed so as to provide any desired alerts or indications as to FES jack and electrode status and performance.

In exemplary embodiments, the FES stimulator wirelessly transmits control signals to FES electrodes for application of FES. The wireless integrated FES system operates comparably as the wired system in coordinating motion of the user's muscles stimulated by the FES system with operation of the device actuator systems of the exoskeleton joint components to ensure appropriate contributions of the two systems similarly as in the previous embodiment. The electrodes could be inductively powered in a manner controlled based on the exoskeleton stimulation settings via the exoskeleton's control electronics, or the electrodes could be outfitted with sufficient programmed intelligence that receive signals requesting stimulation based on stimulation parameters to be used by an implanted stimulator system. Accordingly, integration of a wireless FES system into the exoskeleton device is compatible with using traditional surface skin electrodes, but also with transcutaneous or deeper implanted wireless electrodes. As the wireless configuration lacks specific jacks associated with the electrodes, comparable LED indicators can be provided in the hip component itself, such as along the wing portions of the hip component.

Application of the stimulation may proceed in the wireless configuration comparably as in the previous embodiment. User-specific muscle profile information can be programmed into the exoskeleton control system 20 as part of the exoskeleton control application 26 referenced in FIG. 7. FES stimulation may be applied in a manner timed with the gait for one or both of mobility assistance and therapy to allocate contributions to gait from the user's muscles as stimulated by the FES system versus mobility assistance provided by the joint components of the exoskeleton device. The integrated FES system 90, therefore, likewise provides a synergistic benefit by which the user simultaneously experiences the benefits of both FES and the use of the exoskeleton device.

The wireless integrated FES system also coordinates motion of the user's muscles stimulated by the FES system with operation of the device actuator systems of the exoskeleton joint components to ensure appropriate contributions of the two systems similarly as in the previous embodiment. The electrodes could be inductively powered in a manner controlled based on the exoskeleton stimulation settings via the exoskeleton's control electronics, or the electrodes could be outfitted with sufficient programmed intelligence that receive signals requesting stimulation based on stimulation parameters to be used by an implanted stimulator system. Accordingly, integration of a wireless FES system into the exoskeleton device is compatible with using traditional surface skin electrodes, but also with transcutaneous or deeper implanted wireless electrodes.

An aspect of the invention, therefore, is an enhanced integrated functional electrical stimulation (FES) system that is optimized for integration into an exoskeleton device. In exemplary embodiments, the integrated FES system includes a component of a mobility assistance device, and an FES system mounted within the component of the mobility assistance device. The FES system includes an FES stimulator that is embedded within the component of the mobility assistance device, and a plurality of FES jacks that are electrically connected to the FES stimulator and are located on the component of the mobility assistance device. The FES jacks are configured to receive a plurality of FES electrodes, and an electrical stimulation output from the FES stimulator is conducted through the FES jacks to the FES electrodes. The integrated FES system may include one or more of the following features, either individually or in combination.

In an exemplary embodiment of the integrated FES system, the component of the mobility assistance device comprises a hip component of a legged mobility exoskeleton device including the hip component, a left leg component, and a right leg component.

In an exemplary embodiment of the integrated FES system, the FES stimulator is embedded within a back portion of the hip component, and the FES jacks are located on wing portions of the hip component.

In an exemplary embodiment of the integrated FES system, a first portion of the FES jacks are located on a left wing of the hip component, and a second portion of the FES jacks are located on a right wing of the hip component.

In an exemplary embodiment of the integrated FES system, electrical connections between the FES stimulator and the plurality of FES jacks run internally through the component of the mobility assistance device.

In an exemplary embodiment of the integrated FES system, the FES stimulator is configured as a printed circuit board including a microprocessor that controls the electrical stimulation output from the FES stimulator, and a transformer that modifies the electrical stimulation output to make the electrical stimulation output suitable for stimulation.

In an exemplary embodiment of the integrated FES system, the electrical stimulator further comprises a communications port configured to communicate with electronics of the mobility assistance device to synchronize the electrical stimulation output with actions of at least one component of the mobility assistance device.

In an exemplary embodiment of the integrated FES system, the plurality of FES jacks comprises ten FES jacks corresponding to ten respective channels of electrical stimulation output.

In an exemplary embodiment of the integrated FES system, each of the plurality of FES jacks comprises a cup that contains a light emitting device, and electrical contacts that conduct the electrical stimulation output to the FES electrode that is connected to the respective FES jack.

In an exemplary embodiment of the integrated FES system, the cup is a plastic cup and the light emitting device is a light emitting diode (LED), and the plastic cup is overmolded about the LED.

In an exemplary embodiment of the integrated FES system, the light emitting device is configured to emit light in different ways to provide indications relating to a corresponding FES jack and/or connected electrode.

In an exemplary embodiment of the integrated FES system, each of the plurality of FES jacks includes a lip to provide a secure fit interaction with the component of the mobility assistance device, and flexible tabs that permit a secure connection of the FES electrodes into the respective FES jacks.

In other exemplary embodiments, the integrated FES system has a wireless configuration. In exemplary embodiments incorporating a wireless configuration, the FES system is mounted within the component of the mobility assistance device, the FES system including an FES stimulator that is embedded within the component of the mobility assistance device, and is configured to wirelessly transmit a control signal for applying an electrical stimulation output to a plurality of FES electrodes.

In an exemplary embodiment of the integrated FES system, the component of the mobility assistance device comprises a hip component of a legged mobility exoskeleton device including the hip component, a left leg component, and a right leg component.

In an exemplary embodiment of the integrated FES system, the FES stimulator is embedded within a back portion of the hip component.

In an exemplary embodiment of the integrated FES system, the FES stimulator is configured as a printed circuit board including a microprocessor that controls transmission of the control signal for the electrical stimulation output from the FES stimulator, and a wireless transmitter that wirelessly transmits the control signal.

In an exemplary embodiment of the integrated FES system, the FES system further includes a centralized stimulator and power hub that receives the control signal from the FES stimulator and outputs the electrical stimulation output to the FES electrodes.

In an exemplary embodiment of the integrated FES system, the FES stimulator is configured to transmit the control signal to multiple non-networked distributed of FES electrodes with each FES electrode including embedded power and communication components.

Another aspect of the invention is an enhanced exoskeleton system that incorporates an integrated FES system. In exemplary embodiments, an exoskeleton system includes a legged mobility exoskeleton device including a hip component, a left leg component, and a right leg component, an integrated FES system according to any of the embodiments, and a control system for controlling operation of the exoskeleton device components to selectively configure and modulate hip and knee joint components to perform a gait cycle. The control system is configured to communicate with the FES stimulator of the integrated FES system to synchronize the electrical stimulation output with actions of the exoskeleton device.

Another aspect of the invention is a control method of controlling a mobility assistance device having a plurality of mobility assistance device components including at least one actuator component that drives at least one joint component. In exemplary embodiments, the control method comprises the steps of: providing said mobility assistance device, said mobility assistance device further including a control system for controlling operation of the mobility device components to selectively configure and modulate the at least one joint component; providing within said mobility assistance device a control application to be executed by the control system; providing within said mobility assistance device a plurality of sensors to detect a state of the at least one actuator component and/or the at least one joint component; integrating into said mobility assistance device a functional electrical stimulation (FES) system, wherein the FES system includes an FES stimulator that is embedded within a component of the mobility assistance device; and executing the control application with the control system to perform FES with the FES system in combination with selectively configuring and modulating the at least one joint component. The control method may include one or more of the following features, either individually or in combination.

In an exemplary embodiment of the control method, the FES system includes a plurality of channels for FES, the method further comprising configuring the channels for the stimulation of different muscle groups of a user of the mobility assistance device.

In an exemplary embodiment of the control method, the different muscle groups include a combination of a leg muscle group and a torso muscle group.

In an exemplary embodiment of the control method, the channels are configured to stimulate the different muscle groups in accordance with stance and swing states of muscle groups during a gait of a user of the mobility assistance device.

In an exemplary embodiment of the control method, the FES system includes ten channels for FES that are configurable to stimulate up to sixteen muscle groups.

In an exemplary embodiment of the control method, the control method further includes: providing a mobile device including a mobile application for control of the mobility assistance device; and executing the mobile application with the mobile device to configure the channels of the FES system.

In an exemplary embodiment of the control method, the control method further includes: inputting a muscle profile that is specific to a user of the mobility assistance device; and executing the control application in a manner that is timed with a gait of the user of the mobility assistance device to control a level of contribution of user muscles via FES applied to user muscle groups relative to assistance by the mobility assistance device to the user's gait.

In an exemplary embodiment of the control method, the control method further includes dynamically executing the control application to adjust in real time FES parameters and torque applied by the at least one joint component during the gait of the user.

In an exemplary embodiment of the control method, the FES parameters and torque are adjusted automatically to balance the user's muscle contribution to gait relative to assistance provided by the mobility assistance device.

In an exemplary embodiment of the control method, the at least one joint component is back-drivable and action of the user's muscles by FES reduces torque applied by the at least one joint component.

In an exemplary embodiment of the control method, the control method further includes executing the control application to perform muscle contribution calculations including recording measurements of relative contributions of user muscle groups as stimulated by FES versus assistance by the mobility assistance device to gait.

In an exemplary embodiment of the control method, the control method further includes adjusting FES system operation and joint control of the at least one joint component to optimize user strength and achieving performance goals based on the muscle contribution calculations.

In an exemplary embodiment of the control method, the control method further includes executing the control application to perform a wireless test function whereby FES is provided to a selected muscle group while the user is not walking.

In an exemplary embodiment of the control method, the control method further includes executing the control application to terminate FES with a detection of a connection loss to an FES electrode.

In an exemplary embodiment of the control method, the control method further includes executing the control application to perform a warm-up mode comprising cycling through stimulating muscle groups with the FES system prior to beginning a gait with the exoskeleton device.

In an exemplary embodiment of the control method, the control method further includes executing the control application to generate a continuous-stimulation profile for muscle groups associated with torso region stability, and applying FES in accordance with the continuous-stimulation profile.

In an exemplary embodiment of the control method, the FES stimulator wirelessly transmits control signals to FES electrodes for application of FES.

In an exemplary embodiment of the control method, the mobility assistance device comprises a plurality of indicators respectively corresponding to the plurality of channels for FES, the control method further comprising controlling the indicators to provide different outputs relating to the corresponding channels for FES and related electrodes.

In an exemplary embodiment of the control method, the indicators are light emitting devices that light up in different patters to provide different indications relating to the corresponding channels for FES and related electrodes.

In an exemplary embodiment of the control method, the different indications include one or more of a solid light when a corresponding channel is being stimulated, blinking at a first rate when settings are being modified or a test function is being applied for the corresponding channel, and blinking at a second rate when no complete circuit is detected for the corresponding channel.

Another aspect of the invention is a non-transitory computer readable medium storing program code for a control application for use in controlling a mobility device including at least one drive component that drives at least one joint component; wherein the mobility device comprises: an electronic control system for controlling operation of the at least one drive component to selectively configure and modulate the at least one joint component, and a plurality of sensors to detect a state of the at least one drive component and/or the at least one joint component; and the program code when executed by the electronic control system performs the control method accordingly to any of the embodiments.

Another aspect of the invention a mobility device including an electronic control system for controlling operation of the at least one drive component to selectively configure and modulate the at least one joint component; a plurality of sensors to detect a state of the at least one drive component and/or the at least one joint component; and the non-transitory computer readable medium for performing the control method according to any of the embodiments, wherein the electronic control system executes the program code stored on the non-transitory computer readable medium. The mobility device may be a legged mobility exoskeleton device comprising a plurality of drive components that drive a plurality of joint components including at least knee joint components and hip joint components. The mobility device may be an orthotic device including the at least one drive component that drives the at least one joint component. The mobility device may be a prosthetic device including the at least one drive component that drives the at least one joint component.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An integrated functional electrical stimulation (FES) system comprising:
 a hip component of a legged mobility exoskeleton device that includes the hip component, a left leg component, and a right leg component; and
 an FES system comprising an FES stimulator that is embedded within the hip component of the legged mobility exoskeleton device, and a plurality of FES jacks that are electrically connected to the FES stimulator and are located on the hip component of the legged mobility exoskeleton device;
 wherein the FES jacks are configured to receive a plurality of FES electrodes, and an electrical stimulation output from the FES stimulator is conducted through the FES jacks to the FES electrodes.

2. The integrated FES system of claim 1, wherein the FES stimulator is embedded within a back portion of the hip component and the FES jacks are located on an external surface of the hip component.

3. The integrated FES system of claim 1, wherein electrical connections between the FES stimulator and the plurality of FES jacks run internally through the hip component of the legged mobility exoskeleton device.

4. The integrated FES system of claim 1, wherein the FES stimulator is configured as a printed circuit board including a microprocessor that controls the electrical stimulation output from the FES stimulator, and a transformer that modifies the electrical stimulation output to make the electrical stimulation output suitable for stimulation.

5. The integrated FES system of claim 4, wherein the electrical stimulator further comprises a communications port configured to communicate with electronics of the mobility assistance device to synchronize the electrical stimulation output with actions of at least one component of the mobility assistance device.

6. The integrated FES system of claim 1, wherein the plurality of FES jacks comprises ten FES jacks corresponding to ten respective channels of electrical stimulation output.

7. The integrated FES system of claim 1, wherein each of the plurality of FES jacks comprises a cup that contains a light emitting device, and electrical contacts that conduct the electrical stimulation output to the FES electrode that is connected to the respective FES jack.

8. The integrated FES system of claim 7, wherein the cup is a plastic cup and the light emitting device is a light emitting diode (LED), and the plastic cup is over-molded about the LED.

9. The integrated FES system of claim 7, wherein the light emitting device is configured to emit light in different ways to provide indications relating to a corresponding FES jack and/or connected electrode.

10. The integrated FES system of claim 7, wherein each of the plurality of FES jacks includes a lip to provide a secure fit interaction with the hip component of the legged mobility exoskeleton device, and flexible tabs that permit a secure connection of the FES electrodes into the respective FES jacks.

11. An exoskeleton system comprising:
 the integrated FES system according to claim 1;
 a left leg component and a right leg component; and
 a control system for controlling operation of the hip component, left leg component, and right leg component to selectively configure and modulate hip and knee joint components of the hip component, left leg component, and the right leg component to perform a gait cycle;
 wherein the control system is configured to communicate with the FES stimulator of the integrated FES system to synchronize the electrical stimulation output with actions of the exoskeleton device.

12. A control method of controlling a mobility assistance device having a plurality of mobility assistance device components including at least one actuator component that drives at least one joint component, the control method comprising the steps of:
 providing said mobility assistance device, said mobility assistance device further including a control system for controlling operation of the mobility device components to selectively configure and modulate the at least one joint component;

providing within said mobility assistance device a control application to be executed by the control system;

providing within said mobility assistance device a plurality of sensors to detect a state of the at least one actuator component and/or the at least one joint component;

integrating into a hip component of the mobility assistance device a functional electrical stimulation (FES) system, wherein the FES system includes an FES stimulator that is embedded within the hip component of the mobility assistance device and a plurality of FES jacks that are electrically connected to the FES stimulator and are located on the hip component of the mobility assistance device; and executing the control application with the control system to perform FES with the FES system in combination with selectively configuring and modulating the at least one joint component.

13. The control method of claim 12, wherein the FES system includes a plurality of channels for FES, the method further comprising configuring the channels for the stimulation of different muscle groups of a user of the mobility assistance device.

14. The control method of claim 12, wherein the channels are configured to stimulate the different muscle groups in accordance with stance and swing states of muscle groups during a gait of a user of the mobility assistance device.

15. The control method of claim 12, further comprising:
providing a mobile device including a mobile application for control of the mobility assistance device; and
executing the mobile application with the mobile device to configure the channels of the FES system.

16. The control method of claim 12, further comprising:
inputting a muscle profile that is specific to a user of the mobility assistance device; and
executing the control application in a manner that is timed with a gait of the user of the mobility assistance device to control a level of contribution of user muscles via FES applied to user muscle groups relative to assistance by the mobility assistance device to the user's gait.

17. The control method of claim 16, further comprising dynamically executing the control application to adjust in real time FES parameters and torque applied by the at least one joint component during the gait of the user.

18. The control method of claim 17, wherein the FES parameters and torque are adjusted automatically to balance the user's muscle contribution to gait relative to assistance provided by the mobility assistance device.

19. The control method of claim 15, further comprising executing the control application to perform muscle contribution calculations including recording measurements of relative contributions of user muscle groups as stimulated by FES versus assistance by the mobility assistance device to gait.

20. The control method of claim 19, further comprising adjusting FES system operation and joint control of the at least one joint component to optimize user strength and achieving performance goals based on the muscle contribution calculations.

* * * * *